United States Patent
Wisniewski et al.

(10) Patent No.: US 9,574,001 B2
(45) Date of Patent: Feb. 21, 2017

(54) HUMANIZED SINGLE-CHAIN ANTIBODY AGAINST BETA 3 INTEGRIN FOR THE TREATMENT AND PREVENTION OF METASTASIS

(71) Applicants: Thomas M. Wisniewski, Staten Island, NY (US); Wei Zhang, Shanghai (CN); Suying Dang, Shanghai (CN)

(72) Inventors: Thomas M. Wisniewski, Staten Island, NY (US); Wei Zhang, Shanghai (CN); Suying Dang, Shanghai (CN)

(73) Assignee: New York University, New York, NY (US)

( * ) Notice: Subject to any disclaimer, the term of this patent is extended or adjusted under 35 U.S.C. 154(b) by 392 days.

(21) Appl. No.: 13/958,145

(22) Filed: Aug. 2, 2013

(65) Prior Publication Data
US 2014/0037629 A1    Feb. 6, 2014

Related U.S. Application Data

(60) Provisional application No. 61/678,659, filed on Aug. 2, 2012.

(51) Int. Cl.
*A61K 39/395* (2006.01)
*C07K 16/28* (2006.01)
*A61K 39/00* (2006.01)

(52) U.S. Cl.
CPC ..... *C07K 16/2848* (2013.01); *A61K 2039/505* (2013.01); *C07K 2317/622* (2013.01); *C07K 2317/73* (2013.01)

(58) Field of Classification Search
None
See application file for complete search history.

(56) References Cited

U.S. PATENT DOCUMENTS

| | | | | |
|---|---|---|---|---|
| 7,731,966 | B2 * | 6/2010 | Ni et al. | 424/153.1 |
| 2002/0044936 | A1 * | 4/2002 | Coller et al. | 424/146.1 |
| 2011/0045008 | A1 * | 2/2011 | Karpatkin et al. | 424/179.1 |
| 2011/0052594 | A1 | 3/2011 | Karpatkin et al. | |

OTHER PUBLICATIONS

Artoni et al., Proc Natl Acad Sci U S A. Sep. 7, 2004;101(36):13114-20. Epub Jul. 26, 2004.*
Cohen et al., Pathol Oncol Res. 2000;6(3):163-74.*
Nieswandt et al., Cancer Res. Mar. 15, 1999;59(6):1295-300.*
Amirkhosravi et al., Platelets. 1999;10(5):285-92.*
Li et al., J Biol Chem. Feb. 8, 2008;283(6):3224-30. Epub Dec. 3, 2007.*
Peter et al., Blood. Nov. 1, 1998;92(9):3240-9.*
Amirkhosravi et al., "Inhibition of Tumor Cell-Induced Platelet Aggregation and Lung Metastasis by Oral GpIIb/IIIa Antagonist XV454," Thromb. Haemost. 90:549-54 (2003).
Dang et al., "A Humanized Single-Chain Variable Fragment Antibody Against Beta3 Integrin in *Escherichia coli*," Hybridoma 30(6):543-548 (2011).
Gay & Felding-Habermann, "Contribution of Platelets to Tumour Metastasis," Nature Reviews/Cancer 11:123-134 (2011).
Jain et al., "Platelet Glycoprotein IbAlpha Supports Experimental Lung Metastasis," Proc. Nat'l. Acad. Sci. U.S.A. 104 (21):9024-9028 (2007).
Karpatkin et al., "Role of Adhesive Proteins in Platelet Tumor Interaction In Vitro and Metastasis Formation In Vivo," J. Clin. Invest. 81:1012-1019 (1988).
Karpatkin et al., "Role of Platelets in Tumor Cell Metastases," Ann. N.Y. Acad. Sci. 370:101-118 (1981).
Leclerc, J.R., "Platelet Glycoprotein IIb/IIIa Antagonists: Lessons Learned From Clinical Trials and Future Directions," Crit. Care Med. 30(5)(Suppl.):S332-S340 (2002).
Li et al., "Platelet Fragmentation Requires a Specific Structural Conformation of Human Monoclonal Antibody Against Beta3 Integrin," J. Biol. Chem. 283(6):3224-3230 (2008).
Lonsdorf et al., "Engagement of AlphaIIbBeta3 (GPIIb/IIIa) With AlphaNuBeta3 Integrin Mediates Interaction of Melanoma Cells with Platelets. A Connection to Hematogenous Metastasis" J. Biol. Chem. 287(3):2168-2178 (2012).
Nieswandt et al., "Lysis of Tumor Cells by Natural Killer Cells in Mice Is Impeded by Platelets," Cancer Res. 59:1295-1300 (1999).
Palumbo et al., "Platelets and Fibrin(ogen) Increase Metastatic Potential by Impeding Natural Killer Cell-Mediated Elimination of Tumor Cells," Blood 105:178-185 (2005).
Sierko & Wojtukiewiz, "Inhibition of Platelet Function: Does It Offer a Chance of Better Cancer Progression Control?," Semin. Thromb. Hemost. 33:712-722 (2007).
Trikha et al., "Role of AlphaIIbBeta3 Integrin in Prostate Cancer Metastasis," Prostate 35:185-192 (1998).
Zhang et al., "A Humanized Single-Chain Antibody Against Beta 3 Integrin Inhibits Pulmonary Metastasis by Preferentially Fragmenting Activated Platelets in the Tumor Microenvironment," Blood 120(14):2889-2898 (2012).
Zhang et al., "Dissolution of Arterial Platelet Thrombi in Vivo With a Bifunctional Platelet GPIIIa49-66 Ligand Which Specifically Targets the Platelet Thrombus," Blood 116(13):2336-2344 (2010).
Dang et al., "Dissolution of Pre-Existing Platelet Thrombus by Synergistic Administration of Low Concentrations of Bifunctional Antibodies Against Beta3 Integrin," PLoS ONE 6(10):e27012 (2011).

* cited by examiner

*Primary Examiner* — Michael Szperka
(74) *Attorney, Agent, or Firm* — LeClairRyan, a Professional Corporation

(57) ABSTRACT

The present invention relates to methods inhibiting tumor metastasis and treating cancer in a subject that involve administering to the subject an antibody which recognizes GPIIIa49-66, under conditions effective to inhibit tumor metastasis and/or treat cancer in the subject.

20 Claims, 15 Drawing Sheets

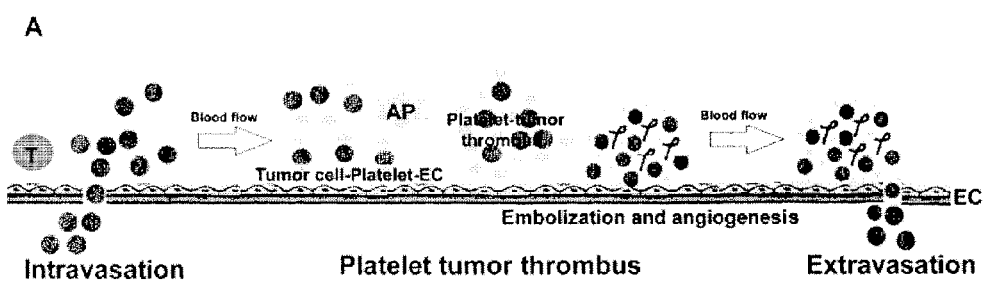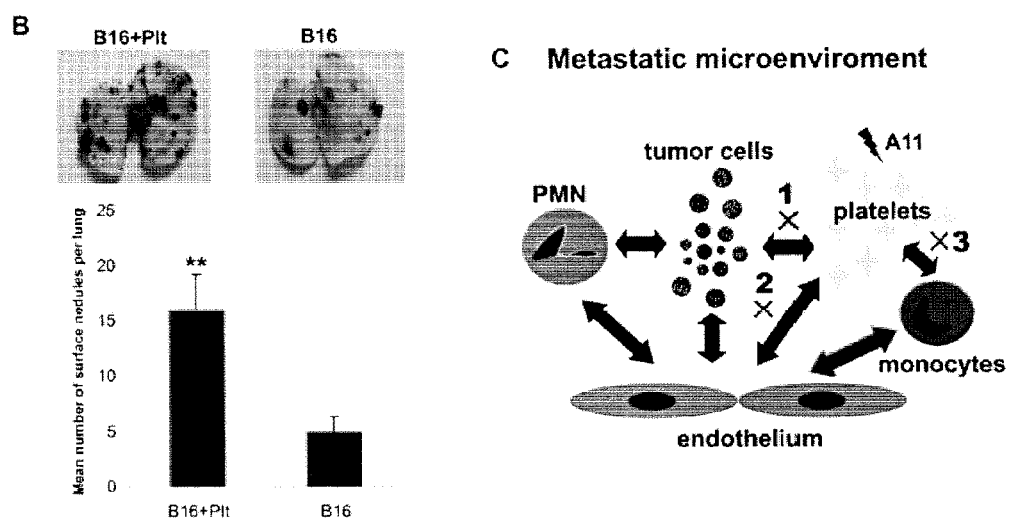
Figures 1A-1C

A

B

SEQUENCE LISTING

```
<160> NUMBER OF SEQ ID NOS: 3

<210> SEQ ID NO 1
<211> LENGTH: 18
<212> TYPE: PRT
<213> ORGANISM: Homo sapiens

<400> SEQUENCE: 1

Cys Ala Pro Glu Ser Ile Glu Phe Pro Val Ser Glu Ala Arg Val Leu
1               5                   10                  15

Glu Asp

<210> SEQ ID NO 2
<211> LENGTH: 384
<212> TYPE: PRT
<213> ORGANISM: Homo sapiens

<400> SEQUENCE: 2

Asn Glu Thr Leu Val Phe Glu Ile Leu Met Gln Gly Lys Asn Pro Gly
1               5                   10                  15

Ile Ala Trp Lys Tyr Ala Leu Pro Lys Val Met Asn Gly Thr Pro Pro
            20                  25                  30
```

```
Ala Thr Lys Arg Pro Ala Tyr Thr Trp Ser Ile Val Gln Ser Glu Cys
         35                  40                  45

Ser Val Ser Cys Gly Gly Tyr Ile Asn Val Lys Ala Ile Cys Leu
 50                  55                  60

Arg Asp Gln Asn Thr Gln Val Asn Ser Ser Phe Cys Ser Ala Lys Thr
 65                  70                  75                  80

Lys Pro Val Thr Glu Pro Lys Ile Cys Asn Ala Phe Ser Cys Pro Ala
                 85                  90                  95

Tyr Trp Met Pro Gly Glu Trp Ser Thr Cys Ser Lys Ala Cys Ala Gly
            100                 105                 110

Gly Gln Gln Ser Arg Lys Ile Gln Cys Val Gln Lys Pro Phe Gln
        115                 120                 125

Lys Glu Glu Ala Val Leu His Ser Leu Cys Pro Val Ser Thr Pro Thr
    130                 135                 140

Gln Val Gln Ala Cys Asn Ser His Ala Cys Pro Pro Gln Trp Ser Leu
145                 150                 155                 160

Gly Pro Trp Ser Gln Cys Ser Lys Thr Cys Gly Arg Gly Val Arg Lys
                165                 170                 175

Arg Glu Leu Leu Cys Lys Gly Ser Ala Ala Glu Thr Leu Pro Glu Ser
            180                 185                 190

Gln Cys Thr Ser Leu Pro Arg Pro Glu Leu Gln Glu Gly Cys Val Leu
        195                 200                 205

Gly Arg Cys Pro Lys Asn Ser Arg Leu Gln Trp Val Ala Ser Ser Trp
    210                 215                 220

Ser Glu Cys Ser Ala Thr Cys Gly Leu Gly Val Arg Lys Arg Glu Met
225                 230                 235                 240

Lys Cys Ser Glu Lys Gly Phe Gln Gly Lys Leu Ile Thr Phe Pro Glu
                245                 250                 255

Arg Arg Cys Arg Asn Ile Lys Lys Pro Asn Leu Asp Leu Glu Glu Thr
            260                 265                 270

Cys Asn Arg Arg Ala Cys Pro Ala His Pro Val Tyr Asn Met Val Ala
        275                 280                 285

Gly Trp Tyr Ser Leu Pro Trp Gln Gln Cys Thr Val Thr Cys Gly Gly
    290                 295                 300

Gly Val Gln Thr Arg Ser Val His Cys Val Gln Gln Gly Arg Pro Ser
305                 310                 315                 320

Ser Ser Cys Leu Leu His Gln Lys Pro Pro Val Leu Arg Ala Cys Asn
                325                 330                 335

Thr Asn Phe Cys Pro Ala Pro Glu Lys Arg Glu Asp Pro Ser Cys Val
            340                 345                 350

Asp Phe Phe Asn Trp Cys His Leu Val Pro Gln His Gly Val Cys Asn
        355                 360                 365

His Lys Phe Tyr Gly Lys Gln Cys Cys Lys Ser Cys Thr Arg Lys Ile
    370                 375                 380

<210> SEQ ID NO 3
<211> LENGTH: 1221
<212> TYPE: PRT
<213> ORGANISM: Homo sapiens

<400> SEQUENCE: 3

Met Glu Cys Ala Leu Leu Leu Ala Cys Ala Phe Pro Ala Ala Gly Ser
1               5                  10                  15

Gly Pro Pro Arg Gly Leu Ala Gly Leu Gly Arg Val Ala Lys Ala Leu
             20                  25                  30
```

Gln Leu Cys Cys Leu Cys Cys Ala Ser Val Ala Ala Ala Leu Ala Ser
            35                  40                  45

Asp Ser Ser Ser Gly Ala Ser Gly Leu Asn Asp Asp Tyr Val Phe Val
 50                  55                  60

Thr Pro Val Glu Val Asp Ser Ala Gly Ser Tyr Ile Ser His Asp Ile
 65                  70                  75                  80

Leu His Asn Gly Arg Lys Lys Arg Ser Ala Gln Asn Ala Arg Ser Ser
                85                  90                  95

Leu His Tyr Arg Phe Ser Ala Phe Gly Gln Glu Leu His Leu Glu Leu
            100                 105                 110

Lys Pro Ser Ala Ile Leu Ser Ser His Phe Ile Val Gln Val Leu Gly
            115                 120                 125

Lys Asp Gly Ala Ser Glu Thr Gln Lys Pro Glu Val Gln Gln Cys Phe
 130                 135                 140

Tyr Gln Gly Phe Ile Arg Asn Asp Ser Ser Ser Val Ala Val Ser
145                 150                 155                 160

Thr Cys Ala Gly Leu Ser Gly Leu Ile Arg Thr Lys Asn Glu Phe
                165                 170                 175

Leu Ile Ser Pro Leu Pro Gln Leu Leu Ala Gln Glu His Asn Tyr Ser
            180                 185                 190

Ser Pro Ala Gly His His Pro His Val Leu Tyr Lys Arg Thr Ala Glu
            195                 200                 205

Glu Lys Ile Gln Arg Tyr Arg Gly Tyr Pro Gly Ser Gly Arg Asn Tyr
 210                 215                 220

Pro Gly Tyr Ser Pro Ser His Ile Pro His Ala Ser Gln Ser Arg Glu
225                 230                 235                 240

Thr Glu Tyr His His Arg Arg Leu Gln Lys Gln His Phe Cys Gly Arg
                245                 250                 255

Arg Lys Lys Tyr Ala Pro Lys Pro Pro Thr Glu Asp Thr Tyr Leu Arg
            260                 265                 270

Phe Asp Glu Tyr Gly Ser Ser Gly Arg Pro Arg Arg Ser Ala Gly Lys
            275                 280                 285

Ser Gln Lys Gly Leu Asn Val Glu Thr Leu Val Val Ala Asp Lys Lys
 290                 295                 300

Met Val Glu Lys His Gly Lys Gly Asn Val Thr Thr Tyr Ile Leu Thr
305                 310                 315                 320

Val Met Asn Met Val Ser Gly Leu Phe Lys Asp Gly Thr Ile Gly Ser
                325                 330                 335

Asp Ile Asn Val Val Val Ser Leu Ile Leu Glu Gln Glu Pro
            340                 345                 350

Gly Gly Leu Leu Ile Asn His His Ala Asp Gln Ser Leu Asn Ser Phe
            355                 360                 365

Cys Gln Trp Gln Ser Ala Leu Ile Gly Lys Asn Gly Lys Arg His Asp
 370                 375                 380

His Ala Ile Leu Leu Thr Gly Phe Asp Ile Cys Ser Trp Lys Asn Glu
385                 390                 395                 400

Pro Cys Asp Thr Leu Gly Phe Ala Pro Ile Ser Gly Met Cys Ser Lys
                405                 410                 415

Tyr Arg Ser Cys Thr Ile Asn Glu Asp Thr Gly Leu Gly Leu Ala Phe
            420                 425                 430

Thr Ile Ala His Glu Ser Gly His Asn Phe Gly Met Ile His Asp Gly
            435                 440                 445

-continued

```
Glu Gly Asn Pro Cys Arg Lys Ala Glu Gly Asn Ile Met Ser Pro Thr
    450                 455                 460
Leu Thr Gly Asn Asn Gly Val Phe Ser Trp Ser Cys Ser Arg Gln
465                 470                 475                 480
Tyr Leu Lys Lys Phe Leu Ser Thr Pro Gln Ala Gly Cys Leu Val Asp
                485                 490                 495
Glu Pro Lys Gln Ala Gly Gln Tyr Lys Tyr Pro Asp Lys Leu Pro Gly
            500                 505                 510
Gln Ile Tyr Asp Ala Asp Thr Gln Cys Lys Trp Gln Phe Gly Ala Lys
        515                 520                 525
Ala Lys Leu Cys Ser Leu Gly Phe Val Lys Asp Ile Cys Lys Ser Leu
530                 535                 540
Trp Cys His Arg Val Gly His Arg Cys Glu Thr Lys Phe Met Pro Ala
545                 550                 555                 560
Ala Glu Gly Thr Val Cys Gly Leu Ser Met Trp Cys Arg Gln Gly Gln
                565                 570                 575
Cys Val Lys Phe Gly Glu Leu Gly Pro Arg Pro Ile His Gly Gln Trp
            580                 585                 590
Ser Ala Trp Ser Lys Trp Ser Glu Cys Ser Arg Thr Cys Gly Gly Gly
        595                 600                 605
Val Lys Phe Gln Glu Arg His Cys Asn Asn Pro Lys Pro Gln Tyr Gly
    610                 615                 620
Gly Leu Phe Cys Pro Gly Ser Ser Arg Ile Tyr Gln Leu Cys Asn Ile
625                 630                 635                 640
Asn Pro Cys Asn Glu Asn Ser Leu Asp Phe Arg Ala Gln Gln Cys Ala
                645                 650                 655
Glu Tyr Asn Ser Lys Pro Phe Arg Gly Trp Phe Tyr Gln Trp Lys Pro
            660                 665                 670
Tyr Thr Lys Val Glu Glu Asp Arg Cys Lys Leu Tyr Cys Lys Ala
        675                 680                 685
Glu Asn Phe Glu Phe Phe Phe Ala Met Ser Gly Lys Val Lys Asp Gly
    690                 695                 700
Thr Pro Cys Ser Pro Asn Lys Asn Asp Val Cys Ile Asp Gly Val Cys
705                 710                 715                 720
Glu Leu Val Gly Cys Asp His Glu Leu Gly Ser Lys Ala Val Ser Asp
                725                 730                 735
Ala Cys Gly Val Cys Lys Gly Asp Asn Ser Thr Cys Lys Phe Tyr Lys
            740                 745                 750
Gly Leu Tyr Leu Asn Gln His Lys Ala Asn Glu Tyr Tyr Pro Val Val
        755                 760                 765
Leu Ile Pro Ala Gly Ala Arg Ser Ile Glu Ile Gln Glu Leu Gln Val
    770                 775                 780
Ser Ser Ser Tyr Leu Ala Val Arg Ser Leu Ser Gln Lys Tyr Tyr Leu
785                 790                 795                 800
Thr Gly Gly Trp Ser Ile Asp Trp Pro Gly Glu Phe Pro Phe Ala Gly
                805                 810                 815
Thr Thr Phe Glu Tyr Gln Arg Ser Phe Asn Arg Pro Glu Arg Leu Tyr
            820                 825                 830
Ala Pro Gly Pro Thr Asn Glu Thr Leu Val Phe Glu Ile Leu Met Gln
        835                 840                 845
Gly Lys Asn Pro Gly Ile Ala Trp Lys Tyr Ala Leu Pro Lys Val Met
850                 855                 860
Asn Gly Thr Pro Pro Ala Thr Lys Arg Pro Ala Tyr Thr Trp Ser Ile
```

```
                865             870             875             880
            Val Gln Ser Glu Cys Ser Val Ser Cys Gly Gly Gly Tyr Ile Asn Val
                            885             890                 895
            Lys Ala Ile Cys Leu Arg Asp Gln Asn Thr Gln Val Asn Ser Ser Phe
                        900                 905                 910
            Cys Ser Ala Lys Thr Lys Pro Val Thr Glu Pro Lys Ile Cys Asn Ala
                        915                 920                 925
            Phe Ser Cys Pro Ala Tyr Trp Met Pro Gly Glu Trp Ser Thr Cys Ser
                        930                 935                 940
            Lys Ala Cys Ala Gly Gly Gln Gln Ser Arg Lys Ile Gln Cys Val Gln
            945                 950                 955                 960
            Lys Lys Pro Phe Gln Lys Glu Ala Val Leu His Ser Leu Cys Pro
                            965                 970                 975
            Val Ser Thr Pro Thr Gln Val Gln Ala Cys Asn Ser His Ala Cys Pro
                        980                 985                 990
            Pro Gln Trp Ser Leu Gly Pro Trp Ser Gln Cys Ser Lys Thr Cys Gly
                        995                 1000                1005
            Arg Gly Val Arg Lys Arg Glu Leu Leu Cys Lys Gly Ser Ala Ala
                1010                1015                1020
            Glu Thr Leu Pro Glu Ser Gln Cys Thr Ser Leu Pro Arg Pro Glu
                1025                1030                1035
            Leu Gln Glu Gly Cys Val Leu Gly Arg Cys Pro Lys Asn Ser Arg
                1040                1045                1050
            Leu Gln Trp Val Ala Ser Ser Trp Ser Glu Cys Ser Ala Thr Cys
                1055                1060                1065
            Gly Leu Gly Val Arg Lys Arg Glu Met Lys Cys Ser Glu Lys Gly
                1070                1075                1080
            Phe Gln Gly Lys Leu Ile Thr Phe Pro Glu Arg Arg Cys Arg Asn
                1085                1090                1095
            Ile Lys Lys Pro Asn Leu Asp Leu Glu Glu Thr Cys Asn Arg Arg
                1100                1105                1110
            Ala Cys Pro Ala His Pro Val Tyr Asn Met Val Ala Gly Trp Tyr
                1115                1120                1125
            Ser Leu Pro Trp Gln Gln Cys Thr Val Thr Cys Gly Gly Gly Val
                1130                1135                1140
            Gln Thr Arg Ser Val His Cys Val Gln Gln Gly Arg Pro Ser Ser
                1145                1150                1155
            Ser Cys Leu Leu His Gln Lys Pro Pro Val Leu Arg Ala Cys Asn
                1160                1165                1170
            Thr Asn Phe Cys Pro Ala Pro Glu Lys Arg Glu Asp Pro Ser Cys
                1175                1180                1185
            Val Asp Phe Phe Asn Trp Cys His Leu Val Pro Gln His Gly Val
                1190                1195                1200
            Cys Asn His Lys Phe Tyr Gly Lys Gln Cys Cys Lys Ser Cys Thr
                1205                1210                1215
            Arg Lys Ile
                1220
```

HUMANIZED SINGLE-CHAIN ANTIBODY AGAINST BETA 3 INTEGRIN FOR THE TREATMENT AND PREVENTION OF METASTASIS

This application claims the priority benefit of U.S. Provisional Patent Application Ser. No. 61/678,659, filed Aug. 2, 2012, which is hereby incorporated by reference in its entirety.

This invention was made with government support under grant number NS073502 awarded by the National Institutes of Health. The government has certain rights in this invention.

FIELD OF THE INVENTION

The present invention relates to methods and compositions for inhibiting metastasis in a subject.

BACKGROUND OF THE INVENTION

Tumor metastasis is the main cause of death from cancer and a major challenge for improving cancer management. Hematogenous tumor cell spreading is a highly complex process, including detachment of cancer cells from the primary site, migration into and transport along the bloodstream, and finally tumor cell arrest and proliferation within distant tissue. Thus survival of tumor cells within the bloodstream and adhesion in the vasculature at the metastatic site are crucial for tumor cell dissemination. Extensive evidence indicates that the interaction of tumor cells with platelets within the bloodstream plays an important role during the early phase of metastasis. (Gay et al., "Contribution of Platelets to Tumour Metastasis," *Nat. Rev. Cancer.* 11(2):123-134 (2011); Labelle et al., "Direct Signaling Between Platelets and Cancer Cells Induces an Epithelial-Mesenchymal-Like Transition and Promotes Metastasis," *Cancer Cell* 20(5):576-590 (2011)).

The involvement of platelets and coagulation factors in hematogenous tumor metastasis has long been recognized. Cancer patients frequently present with signs of thrombosis, and these are most severe if the disease has progressed to a metastatic stage (Gay et al., "Contribution of Platelets to Tumour Metastasis," *Nat. Rev. Cancer.* 11(2):123-134 (2011); Labelle et al., "Direct Signaling Between Platelets and Cancer Cells Induces an Epithelial-Mesenchymal-Like Transition and Promotes Metastasis," *Cancer Cell* 20(5): 576-590 (2011); Tomita et al., "Prognostic Impact of Thrombocytosis in Resectable Non-Small Cell Lung Cancer," *Interact. Cardiovasc. Thorac. Surg.* 7(4):613-615 (2008); Suppiah et al., "Thrombocytosis as a Prognostic Factor for Survival in Patients with Metastatic Renal Cell Carcinoma," *Cancer* 107(8):1793-1800 (2006); Ayhan et al., "The Value of Preoperative Platelet Count in the Prediction of Cervical Involvement and Poor Prognostic Variable in Patients with Endometrial Carcinoma," *Gynecol. Oncol.* 103(3):902-905 (2006); Shimada et al., "Thrombocytosis Associated with Poor Prognosis in Patients with Esophageal Carcinoma," *J. Am. Coll. Surg.* 198(5):737-741 (2004); Borsig, L., "The Role of Platelet Activation in Tumor Metastasis," *Expert Rev. Anticancer Ther.* 8(8):1247-1255 (2008)). Furthermore, thrombocytopenia or the inhibition of platelet function can markedly suppress tumor metastasis (Francis et al., "Effect of Antihemostatic Agents on Experimental Tumor Dissemination," *Semin. Thromb. Hemost.* 28(1):29-38 (2002); Amirkhosravi et al., "Blockage of GPIIb/IIIa Inhibits the Release of Vascular Endothelial Growth Factor (VEGF) From Tumor Cell-Activated Platelets and Experimental Metastasis," *Platelets* 10(5):285-292 (1999); Troxler et al., "Platelet Function and Antiplatelet Therapy," *Br. J. Surg.* 94(6):674-682 (2007); Rothwell et al., "Effect of Daily Aspirin on Risk of Cancer Metastasis: A Study of Incident Cancers During Randomized Controlled Trials," *Lancet* 379(9826):1591-1601 (2012)). Subsequent animal models in which specific platelet functions were altered through drug treatment or controlled genetic ablation have led to a model of platelet supported tumor metastasis in which tumor cells enter the bloodstream (intravasation), and bind and activate platelets (cohesion) and leukocytes (Sierko et al., "Inhibition of Platelet Function: Does it Offer a Chance of Better Cancer Progression Control?" *Semin. Thromb. Hemost.* 33(7):712-721 (2007); Trikha et al., "Role of AlphaII(b)beta3 Integrin in Prostate Cancer Metastasis," *Prostate* 35(3):185-192 (1998)). These host cells then assist tumour cell arrest at the vessel wall (adhesion) and survival within the vasculature (immune evasion), which enables exit from the circulation (extravasation), and tumour cell survival and proliferation within target tissues of metastasis (Jain et al., "Platelet Glycoprotein Ib (alpha) Supports Experimental Lung Metastasis," *Proc. Natl. Acad. Sci. U.S.A.* 104(21):9024-9028 (2007); Nieswandt et al., "Lysis of Tumor Cells by Natural Killer Cells in Mice is Impeded by Platelets," *Cancer Res.* 59(6):1295-1300 (1999); Palumbo et al., "Platelets and Fibrinogen Increase Metastatic Potential by Impeding Natural Killer Cell-Mediated Elimination of Tumor Cells," *Blood* 105(1):178-185 (2005)). These contributions of platelets to tumour cell survival and spread suggest that agents directed against these processes may give rise to new therapies for patients with a high risk of metastasis or for minimizing the risk of cancer cell dissemination during tumor surgery.

The present invention is directed at overcoming this and other deficiencies in the art.

SUMMARY OF THE INVENTION

A first aspect of the present invention is directed to a method of inhibiting tumor metastasis in a subject. This method involves selecting a subject with a tumor and administering to the selected subject an antibody or binding portion thereof which recognizes GPIIIa49-66 under conditions effective to inhibit tumor metastasis.

Another aspect of the present invention is directed to a method for treating cancer in a subject. This method involves selecting a subject with cancer and administering to the selected subject an effective amount of an antibody or binding portion thereof which recognizes GPIIIa49-66 under conditions effective to treat the cancer.

Integrin αIIbβ3 (platelet glycoprotein GPIIb/IIIa) is a heterodimeric receptor of the integrin family expressed at high density (50,000-80,000 copies/cell) on the platelet membrane (Shattil et al., "Perspectives Series: Cell Adhesion in Vascular Biology. Integrin Signaling in Vascular Biology," *J. Clin. Invest.* 100 (1):1-5 (1997), which is hereby incorporated by reference in its entirety). In circulation it is normally in a resting state but is activated during platelet aggregation and adhesion, which in binding to fibrinogen and von Willebrand factor allows formation of a platelet aggregate or a mural thrombus on damaged vessel walls (Suppiah et al., "Thrombocytosis as a Prognostic Factor for Survival in Patients with Metastatic Renal Cell Carcinoma," *Cancer* 107(8):1793-1800 (2006), which is hereby incorporated by reference in its entirety). GPIIIa49-66 (CAPESIEF-PVSEARLED; SEQ ID NO: 1) is a linear epitope of integrin subunit β3 (GPIIIa) on the surface of platelets. A unique antiplatelet autoantibody was previously identified in patients with HIV- or hepatitis C related thrombocytopenia that recognizes the sequence GPIIIa49-66 and induces complement-independent platelet lysis by generation of reactive oxygen species and peroxide after platelet-reduced nicotinamide adenine dinucleotide phosphate oxidase activation (Nardi et al., "Complement-Independent Peroxide-Induced Antibody Lysis of Platelets in HIV-1-Related Immune Thrombocytopenia," *Cell* 106(5):551-561 (2001); Nardi et al., "Complement-Independent Ab-Induced Peroxide Lysis of Platelets Requires 12-Lipoxygenase and a Platelet NADPH Oxidase Pathway," *J. Clin. Invest.* 113(7): 973-980 (2004); Li et al., "Role of Molecular Mimicry to HIV-1 Peptides in HIV-1 Related Immunologic Thrombocytopenia," *Blood* 106(2):572-576 (2005); Zhang et al., "Specific Cross-Reaction of Anti-dsDNA Antibody with Platelet Integrin GPIIIa49-66," *Autoimmunity* 43(8):682-689 (2010); Zhang et al., "Role of Molecular Mimickry of Hepatitis C (HCV) Protein with Platelet GPIIIa in Hepatitis C-Related Thrombocytopenia," *Blood* 113(17):4086-4093 (2009), which are hereby incorporated by reference in their entirety). By screening a human single-chain fragment variable region (scFv) library with the GPIIIa49-66 peptide as bait, a human monoclonal scFv Ab was identified that recognizes GPIIIa49-66 (named A11) and has similar functional properties to the patient autoantibody in that it preferentially binds to activated platelets and can lyse platelet thrombus in vitro (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010); Li et al., "Platelet Fragmentation Requires a Specific Structural Conformation of Human Monoclonal Antibody Against beta3 Integrin," *J. Biol. Chem.* 283(6):3224-3230 (2008); Dang et al., "A Humanized Single-Chain Variable Fragment Antibody Against beta3 Integrin in *Escherichia coli*," *Hybridoma* 30(6):543-548 (2011), which are hereby incorporated by reference in their entirety). As demonstrated herein, the A11 antibody significantly inhibits the development of pulmonary metastasis in the Lewis lung carcinoma (LLC) metastatic model by decreasing the mean number of surface nodules and mean volume of pulmonary nodules. The A11 antibody protects against lung metastases in a time window that extends 4 hours prior to and 4 hours after the injection of LLC cells. Thus, targeting the GPIIIa49-66 epitope of integrin subunit β3 (GPIIIa) with a humanized anti-GPIIIa49-66 antibody or other targeting agent provides a novel anti-metastatic strategy through lysing activated platelets in the tumor microenvironment.

BRIEF DESCRIPTION OF THE DRAWINGS

FIGS. 1A-1C depict anti-platelet GPIIIa49-66 scFv Ab (A11) properties for the inhibition of tumor metastasis. FIG. 1A is a schematic representation summarizing the events occurring following tumor intravasation, tumor platelet-endothelial cell binding and platelet-tumor thrombus formation, tumor-platelet embolization, angiogenesis, and extravasation. "T", refers to tumor cells; "AP", activated platelets. FIG. 1B shows platelets promoting metastases in an experimental pulmonary metastasis B16 tumor model. The upper row of images are of lung specimens with metastatic colonies. "Plt", refers to platelet. The graph of FIG. 1B denotes numeric results of surface pulmonary nodules (n=8, **p<0.01). FIG. 1C is a schematic representation of the hypothesized mechanisms of A11 inhibition of tumor metastasis involving activated platelet lysis within the tumor microenvironment.

FIG. 2A illustrates the treatment protocol utilizing the LLC spontaneous lung metastasis model. FIG. 2B is a graph showing the mean number of surface nodules per lung in animals administered the human monoclonal scFv Ab against GPIIIa49-66 (A11) or control scFv Ab (13CG2). FIG. 2C is a graph showing the mean volume of nodules per lung in these same animals. FIG. 2D shows representative histologic evidence from tumor sections of the A11 and 13CG2 antibody treatment groups. FIG. 3D(a-b) 13CG2 treated (×40) (a), and (×200) (b); FIG. 3D(c-d) A11 treated (×40) (c), and (×200) (d), n=8, *p<0.01.

FIG. 3A shows the preventive (a, b) and therapeutic (c, d, e) treatment protocols used in the lung metastasis model. "i.v." represents intravenous injection. FIG. 3B is a graph showing the mean number of surface nodules per lung in the different treatment groups. FIG. 3C is a graph showing the mean volume of nodules per lung in the different treatment groups. n=8/group, **P<0.001, *P<0.01, Ctrl. refers to control scFv Ab 13CG2.

FIG. 4A shows the mean number of surface nodules per lung, and FIG. 4B shows the mean volume of nodules per lung. FIG. 4C is a graph showing the induction of platelet count drop as determined at different time points. n=8, * refers to values with significant differences, n.s. refers to no significant difference.

FIG. 5A are fluorescent microscopy images of frozen lung tissue section (20×) showing B16 loci within the lungs following 13CG2 control antibody (left image) or A11 antibody treatment (right image). FIG. 5B is a graph depicting the quantitative assessment of adhesion of B16 cells in lung tissue of 13CG2 and A11 antibody treated animals based on measurement of fluorescent intensity under a fluorescence plate reader. n=5, *p<0.01.

FIGS. 6A and 6B show the effect of A11 on the adhesion of tumor cells to platelets in vitro. FIG. 6A are fluorescent images showing the adhesion of LLC cells to activated platelets as observed under fluorescence microscope, and FIG. 6B is a quantitative analysis of the adhesion of LLC cells to activated platelets in the presence of various concentrations of A11 or 13CG2 antibodies. The quantitative assessment was based on measurements of fluorescent intensity under a fluorescence plate reader. The experiment was repeated three times and each antibody concentration was tested in four separate wells. FIG. 6C shows the effect of A11 on the adhesion of platelets to human umbilical endothelial cell (HUVECs) in vitro. The extent of adhesion was expressed as the percentage of control platelets adhering without preincubation with A11 or control scFv (13CG2). The experiment was repeated three times and each antibody concentration was tested in four separate wells. FIGS. 6D and 6E show the effect of A11 on platelet mediated tumor cell adhesion to endothelial cells in vitro. B16 melanoma cells adhesion to HUVECs was performed as described in the Examples. The adhesion efficiency of B16 tumor cell in the presence of A11 (right image) or 13CG2 (left image) antibodies, respectively, was observed under a fluorescence microscope (FIG. 6D). A quantitative measurement of B16 melanoma cell adhesion to HUVECs is shown in the graph of FIG. 6E. FIG. 6F shows the effect of A11 antibody or 13CG2 control antibody on the destruction of already formed tumor-platelet aggregates. Data and SD are given for 3 separate experiments at 0.5 µM reagent in which each time point represents 5 measurements.

FIG. 8A-8C show the effect of A11 on the viability of B16 cells (FIG. 8A), LLC cells (FIG. 8B), and HUVEC (FIG. 8C) as evaluated by the MTT assay. Data are mean±SD of three different determinations. FIG. 8D shows the effect of A11 antibody on the chemotaxis of tumor cells and HUVECs. Chemotaxis was performed in Transwell plates as described in the Examples. Data and SD are given for 3 independent experiment results in which each concentration represents 4 measurements. FIG. 8E shows the effect of A11 on LLC s.c. tumor growth. Tumor dimensions were measured with calipers for calculation of tumor volume. n=5, error bars indicate SD.

FIG. 9A is a panel of fluorescent microscopy images of HUVEC tube formation. Proliferating HUVECs were plated on the surface of Matrigel in complete media with the indicated doses of A11 or control scFv Ab (13CG2). Sulforaphane at 2.5 µM acts as a control inhibitor of tube formation. Tube formation was evaluated 10 hours later. Representative tube formations are from three independent experiments. FIG. 9B provides a quantitative assessment of HUVEC tube formation. The PBS-treated controls (n=3) were normalized to 100%. % Controls (n=3) from drug-treated groups. Columns represent mean; bars indicate standard deviation (n=3). *p<0.05 versus PBS-treated control.

FIG. 10A are images of representative Matrigel plugs that contained no VEGF (control), VEGF alone, or VEGF plus A11 (50 µg). FIG. 10B provides a quatitative assessment of blood vessel growth based on measurement of hemoglobin in the Matrigel. Five mice were used per group, and the experiments were repeated twice. The data are presented as mean; bars, ±SD. *p<0.05 versus Matrigel alone. n.s. refers to no significant difference.

FIG. 11A shows the effect of A11 on platelet count drop at different time points. Purified control scFv 13CG2 and A11 were injected intravenously into C57/BL6 mice, and platelet counts followed for 24 hours. Results are the mean±SD of two independent experiments, which were performed using 4 animals for each treatment. FIG. 11B shows the effect of A11 on mouse bleeding time. C57/BL6 mice were intravenously injected with control scFv 13CG2 (n=23) or A11 (n=28), and their bleeding time was monitored 4 hours later; horizontal bars represent median tail bleeding time.

DETAILED DESCRIPTION OF THE INVENTION

Figures 2A, 2B, 2C, 2D:
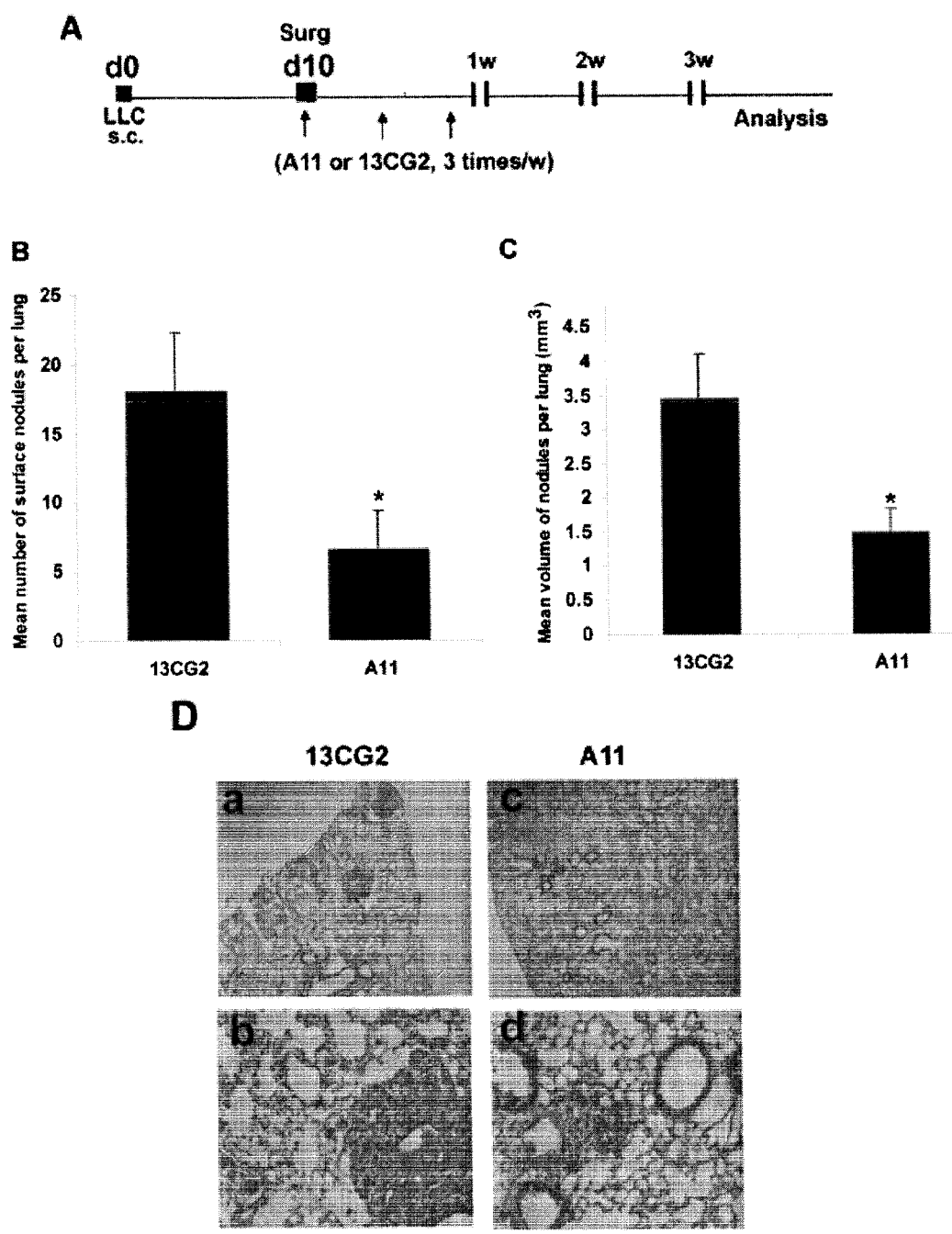
FIGS. 2A-2D show the effect of A11 on spontaneous metastasis of Lewis Lung Carcinoma (LLC).

A first aspect of the present invention is directed to a method of inhibiting tumor metastasis in a subject. This method involves selecting a subject with a tumor and administering to the selected subject an antibody or binding portion thereof which recognizes GPIIIa49-66 under conditions effective to inhibit tumor metastasis.

In accordance with this aspect of the invention, tumor metastasis encompasses the spread of a tumor from one organ or site in the body, i.e., the primary site of disease or primary tumor, to another organ or site in the body. Typically, a metastatic tumor is one that spreads from a primary organ or site to another, non-adjacent, organ or site in the body. Virtually all cancers have the potential to metastasize. Accordingly, a subject at risk for metastatic disease or tumor metastasis is any subject having a primary tumor.

The metastases may occur to any site, however some cancers preferentially metastasize to particular organs. For example, lung, breast, head and neck, cervical, and bladder tumors frequently metastasize to particular organs. Specifically, lung cancer metastasizes to brain, bone, liver, adrenal glands, pleura, subcutaneous tissue, kidney, lymph nodes, cerebrospinal fluid, pancreas, and/or bone marrow. Breast cancer metastasizes to lymph nodes, breast, abdominal viscera, lungs, bones, liver, adrenal glands, brain, meninges, pleura, and/or cerebrospinal fluid. Head and neck cancer metastasizes to lung, esophagus, upper digestive tracts, lymph nodes, and/or the oral and nose cavity. Cervical cancer metastasizes to bladder, rectum, pelvic wall, lymph nodes, and/or paracervical spaces. Bladder cancer metastasizes to the prostate, uterus, vagina, bowel, pelvic wall, lymph nodes, and/or perivesical fat.

The methods of the present invention are suitable for the inhibition and/or treatment of any type of tumor metastasis. Metastatic diseases particularly suitable for inhibition and/or treatment in accordance with the methods of the present invention include, without limitation, metastatic breast cancer, metastatic gastrointestinal cancer, metastatic kidney (renal) cancer, metastatic lung cancer, metastatic brain cancer, metastatic pancreatic cancer, metastatic ovarian cancer, metastatic colorectal cancer, metastatic prostate cancer, metastatic liver cancer, metastatic melanoma, and metastatic pediatric cancers (e.g., medulloblastoma).

Another aspect of the present invention is directed to a method for treating cancer in a subject. This method involves selecting a subject with cancer and administering to the selected subject an effective amount of an antibody or binding portion thereof which recognizes GPIIIa49-66 under conditions effective to treat the cancer.

In accordance with this aspect of the present invention, cancers suitable for treatment include, without limitation, breast cancer, gastrointestinal tract cancer, kidney (renal) cancer, lung cancer, liver cancer, prostate cancer, brain cancer, pancreatic cancer, ovarian cancer, colorectal cancer, melanoma, and pediatric cancers.

In the context of treating cancer, a therapeutically effective amount of a GPIIIa49-66 targeting agent of the present invention is the amount necessary to reduce, slow, or inhibit the tumor growth or tumor cell proliferation and expansion. Treating cancer encompasses any improvement in the cancerous condition, for example, slowing progression and/or development of the disease.

As used herein, a "subject" or "patient" encompasses any animal, but preferably a mammal. More preferably, the subject or patient is a human. In all aspects of the invention, a subject or patient is selected for treatment based on a positive cancer diagnosis, their risk of developing metastatic disease, a positive metastatic disease diagnosis, and/or their suitability for responding to an antibody or other therapeutic targeting agent which recognizes the GPIIIa49-66 epitope of GPIIIa.

Integrin αIIbβ3 (platelet glycoprotein GPIIb/IIIa) is a heterodimeric receptor of the integrin family expressed at high density (50,000-80,000 copies/cell) on the platelet membrane (Shattil et al., "Perspectives Series: Cell Adhesion in Vascular Biology. Integrin Signaling in Vascular Biology," *J. Clin. Invest.* 100 (1):1-5 (1997), which is hereby incorporated by reference in its entirety). In circulation it is normally in a resting state but is activated during platelet aggregation and adhesion, which in binding to fibrinogen and von Willebrand factor allows formation of a platelet aggregate or a mural thrombus on damaged vessel walls. GPIIIa(49-66) is a linear epitope of the integrin subunit β3 (GPIIIa), having the amino acid sequence of CAPESIEFPVSEARVLED (SEQ ID NO: 1) that is expressed on the surface of platelets (Morris et al., "Autoimmune Thrombocytopenic Purpura in Homosexual Men," *Ann Intern Med* 96:714-717 (1982); Najean et al., "The Mechanism of Thrombocytopenia in Patients with HIV Infection," *J Lab Clin Med* 123(3):415-20 (1994), which are hereby incorporated by reference in their entirety).

Suitable therapeutic agents for inhibiting tumor metastasis and/or treating cancer in a subject include any GPIIIa (49-66)-specific targeting agent. In one embodiment of the present invention, the GPIIIa(49-66)-specific targeting agent is an isolated anti-platelet integrin GPIIIa(49-66) antibody. This antibody induces complement-independent platelet oxidative fragmentation and death by generation of platelet peroxide following NADPH oxidase activation. GPIIIa(49-66)-specific antibodies exhibit one or more desirable properties, such as high affinity binding for GPIIIa(49-66), the ability to induce complement-independent platelet oxidative fragmentation and platelet death.

In another embodiment of the present invention, the GPIIIa(49-66)-specific targeting agent is an endogenous C-terminal 385 amino acid fragment of ADAMTS-18 protein (AD-18F) with the following amino acid sequence (SEQ ID NO: 2):

```
  1 NETLVFEILM QGKNPGIAWK YALPKVMNGT PPATKRPAYT WSIVQSECSV SCGGGYINVK

61 AICLRDQNTQ VNSSFCSAKT KPVTEPKICN AFSCPAYWMP GEWSTCSKAC AGGQQSRKIQ

121 CVQKKPFQKE EAVLHSLCPV STPTQVQACN SHACPPQWSL GPWSQCSKTC GRGVRKRELL

181 CKGSAAETLP ESQCTSLPRP ELQEGCVLGR CPKNSRLQWV ASSWSECSAT CGLGVRKREM

241 KCSEKGFQGK LITFPERRCR NIKKPNLDLE ETCNRRACPA HPVYNMVAGW YSLPWQQCTV

301 TCGGGVQTRS VHCVQQGRPS SSCLLHQKPP VLRACNTNFC PAPEKREDPS CVDFFNWCHL

361 VPQHGVCNHK FYGKQCCKSC TRKI
```

ADAMTS-18 protein has the following amino acid sequence (SEQ ID NO: 3):

```
  1 MECALLLACA FPAAGSGPPR GLAGLGRVAK ALQLCCLCCA SVAAALASDS SSGASGLNDD

61 YVFVTPVEVD SAGSYISHDI LHNGRKKRSA QNARSSLHYR FSAFGQELHL ELKPSAILSS

121 HFIVQVLGKD GASETQKPEV QQCFYQGFIR NDSSSSVAVS TCAGLSGLIR TRKNEFLISP

181 LPQLLAQEHN YSSPAGHHPH VLYKRTAEEK IQRYRGYPGS GRNYPGYSPS HIPHASQSRE

241 TEYHHRRLQK QHFCGRRKKY APKPPTEDTY LRFDEYGSSG RPRRSAGKSQ KGLNVETLVV

301 ADKKMVEKHG KGNVTTYILT VMNMVSGLFK DGTIGSDINV VVVSLILLEQ EPGGLLINHH

361 ADQSLNSFCQ WQSALIGKNG KRHDHAILLT GFDICSWKNE PCDTLGFAPI SGMCSKYRSC

421 TINEDTGLGL AFTIAHESGH NFGMIHDGEG NPCRKAEGNI MSPTLTGNNG VFSWSSCSRQ

481 YLKKFLSTPQ AGCLVDEPKQ AGQYKYPDKL PGQIYDADTQ CKWQFGAKAK LCSLGFVKDI

541 CKSLWCHRVG HRCETKFMPA AEGTVCGLSM WCRQGQCVKF GELGPRPIHG QWSAWSKWSE

601 CSRTCGGGVK FQERHCNNPK PQYGGLFCPG SSRIYQLCNI NPCNENSLDF RAQQCAEYNS

661 KPFRGWFYQW KPYTKVEEED RCKLYCKAEN FEFFFAMSGK VKDGTPCSPN KNDVCIDGVC

721 ELVGCDHELG SKAVSDACGV CKGDNSTCKF YKGLYLNQHK ANEYYPVVLI PAGARSIEIQ

781 ELQVSSSYLA VRSLSQKYYL TGGWSIDWPG EFPFAGTTFE YQRSFNRPER LYAPGPTNET

841 LVFEILMQGK NPGIAWKYAL PKVMNGTPPA TKRPAYTWSI VQSECSVSCG GGYINVKAIC

901 LRDQNTQVNS SFCSAKTKPV TEPKICNAFS CPAYWMPGEW STCSKACAGG QQSRKIQCVQ
```

```
 961 KKPFQKEEAV LHSLCPVSTP TQVQACNSHA CPPQWSLGPW SQCSKTCGRG VRKRELLCKG

1021 SAAETLPESQ CTSLPRPELQ EGCVLGRCPK NSRLQWVASS WSECSATCGL GVRKREMKCS

1081 EKGFQGKLIT FPERRCRNIK KPNLDLEETC NRRACPAHPV YNMVAGWYSL PWQQCTVTCG

1141 GGVQTRSVHC VQQGRPSSSC LLHQKPPVLR ACNTNFCPAP EKREDPSCVD FFNWCHLVPQ

1201 HGVCNHKFYG KQCCKSCTRK I
```

ADAMTS-18 is a disintegrin metalloproteinase with thrombospondin-like motifs at its C-terminal end. The 385 amino acid fragment of ADAMTS-18 (AD-18F) was identified using a peptide phage display library and GPIIIa(49-66) of the platelet integrin GPIIIa as the bait (Li et al., "C-terminal ADAMTS-18 Fragment Induces Oxidative Platelet Fragmentation, Dissolves Platelet Aggregates and Protects Against Carotid Artery Occlusion and Cerebral Stroke," *Blood* 113 (24): 6051-6060 (2009), which is hereby incorporated by reference in its entirety).

ADAMTS-18 is secreted and cleaved following thrombin activation (damage) of endothelial cells. It induces oxidative platelet fragmentation in an identical kinetic fashion as anti-GPIIIa(49-66) antibody. Thrombin produces a 45 kD terminal fragment similar to the ADAMTS-18, 385 amino acid fragment (i.e. AD-18F) (SEQ ID NO:2). AD-18F fragment also displays the desirable properties such as high affinity binding for GPIIIa(49-66), the ability to induce complement-independent platelet oxidative fragmentation and platelet death. This fragment, AD-18F, is an important endogenous regulator of arterial platelet thrombus formation, because an antibody against it, shortens the mouse tail vein bleeding time (Li et al., "C-terminal ADAMTS-18 Fragment Induces Oxidative Platelet Fragmentation, Dissolves Platelet Aggregates and Protects Against Carotid Artery Occlusion and Cerebral Stroke," *Blood* 113 (24): 6051-6060 (2009), which is hereby incorporated by reference in its entirety). Similar proteins or peptides with the ability to induce complement-independent platelet oxidative fragmentation and platelet death can be identified using the peptide phage display library and GPIIIa(49-66) as bait.

The antibodies and proteins of the present invention include "binding portions" of the antibodies and proteins described above. A "binding portion" is a fragment, variant, analog, or chemical derivative of the subject antibody or protein, which terms are defined below. A binding portion retains at least a part of the amino acid sequence of the antibody or protein of interest, which permits its utility in accordance with the present invention. This specificity can readily be quantified by means of the techniques disclosed in the present invention and also by techniques known to those of skill in the art.

A "fragment" of the antibodies and proteins disclosed herein refers to any subset of the molecule, that is, a shorter peptide or antibody binding portion as described herein.

A "variant" of the antibodies or protein fragments described herein refers to a molecule which is substantially similar either to the entire antibody or protein or a fragment thereof. Variant peptides may be conveniently prepared by direct chemical synthesis of the variant peptide, using methods well known in the art. Alternatively, amino acid sequence variants of the antibodies and proteins of the present invention can be prepared by mutations in DNA molecules which encode the antibody or protein of interest. Such variants include, for example, deletions, insertions, or substitutions of residues within the amino acid sequences of the GPIIIa(49-66) targeting antibody or protein. Any combination of deletion, insertion, and substitution may be made to arrive at the final construct, provided that the final construct possesses the desired activity.

An "analog" of the antibodies or protein fragments of the present invention refers to a non-natural molecule which is substantially similar to either the entire antibody or peptide or to an active fragment thereof.

A "chemical derivative" of the antibodies or protein fragments of the present invention contains additional chemical moieties which are not normally part of the amino acid sequence of the antibody. Covalent modifications of the amino acid sequence are included within the scope of this invention. Such modifications may be introduced into the antibody or protein derivatives by reacting targeted amino acid residues from the protein with an organic derivatizing agent that is capable of reacting with selected side chains or terminal residues.

As used herein, the term "antibody" is meant to include intact immunoglobulins derived from natural sources or from recombinant sources, as well as immunoreactive portions (i.e., binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies, and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli,*" *Proc Natl Acad Sci USA* 85:5879-5883 (1988); Bird et al, "Single-Chain Antigen-Binding Proteins," *Science* 242:423-426 (1988), which are hereby incorporated by reference in their entirety).

Naturally occurring antibodies typically have two identical heavy chains and two identical light chains, with each light chain covalently linked to a heavy chain by an interchain disulfide bond and multiple disulfide bonds further link the two heavy chains to one another. Individual chains can fold into domains having similar sizes (110-125 amino acids) and structures, but different functions. The light chain can comprise one variable domain (VL) and/or one constant domain (CL). The heavy chain can also comprise one variable domain (VH) and/or, depending on the class or isotype of antibody, three or four constant domains (CH1, CH2, CH3 and CH4). In humans, the isotypes are IgA, IgD, IgE, IgG, and IgM, with IgA and IgG further subdivided into subclasses or subtypes (IgA1-2 and IgG1-4).

Generally, the variable domains show considerable amino acid sequence variability from one antibody to the next, particularly at the location of the antigen-binding site. Three regions, called hyper-variable or complementarity-determining regions (CDRs), are found in each of VL and VH, which are supported by less variable regions called framework variable regions. The inventive antibodies include IgG monoclonal antibodies as well as antibody fragments or engineered forms. These are, for example, Fv fragments, or proteins wherein the CDRs and/or variable domains of the exemplified antibodies are engineered as single-chain antigen-binding proteins.

The portion of an antibody consisting of the VL and VH domains is designated as an Fv (Fragment variable) and constitutes the antigen-binding site. A single chain Fv (scFv or SCA) is an antibody fragment containing a VL domain and a VH domain on one polypeptide chain, wherein the N terminus of one domain and the C terminus of the other domain are joined by a flexible linker. The peptide linkers used to produce the single chain antibodies are typically flexible peptides, selected to assure that the proper three-dimensional folding of the VL and VH domains occurs. The linker is generally 3 to 50 amino acid residues, and in some cases is shorter, e.g., about 3 to 30 amino acid residues, or 3 to 25 amino acid residues, or even 3 to 15 amino acid residues. An example of such linker peptides includes repeats of four glycine residues followed by a serine residue.

Single chain antibodies lack some or all of the constant domains of the whole antibodies from which they are derived. Therefore, they can overcome some of the problems associated with the use of whole antibodies. For example, single-chain antibodies tend to be free of certain undesired interactions between heavy-chain constant regions and other biological molecules. Additionally, single-chain antibodies are considerably smaller than whole antibodies and can have greater permeability than whole antibodies, allowing single-chain antibodies to localize and bind to target antigen-binding sites more efficiently. Furthermore, the relatively small size of single-chain antibodies makes them less likely to provoke an unwanted immune response in a recipient than whole antibodies.

In one embodiment of the present invention, the GPIIIa (49-66) targeting agent is a single chain monoclonal antibody ("scFv") possessing properties described above. Suitable human scFv monoclonal antibodies against GPIIIa(49-66) which induce platelet fragmentation have been identified using phage display (Li et al., "Platelet Fragmentation Requires a Specific Structural Conformation of Human Monoclonal Antibody against beta3 Integrin," *J Biol Chem* 2008; 283:3224-30 (2008), which is hereby incorporated by reference in its entirety). Of these identified antibodies, the monoclonal scFv antibodies are also capable of destroying platelet aggregates. Often, in order to clinically use antibody induced binding and oxidative platelet fragmentation, a monoclonal antibody is required, because some polyclonal antibodies have cross-reactivity with other antigens. A phage surface display antibody technology system can be successfully used to screen single chain antibodies against GPIIIa (49-66).

In addition to scFv antibodies, the present invention encompasses other binding portions or fragments of whole antibodies. Such binding portions include the F(ab')$_2$, F(ab)$_2$, Fab', Fab, Fv, sdAb (nanobody), Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Single-domain antibodies (sdAb; nanobody) are antibody fragments consisting of a single monomeric variable antibody domain (~12-15 kDa). The sdAb are derived from the variable domain of a heavy chain ($V_H$) or the variable domain of a light chain ($V_L$). sdAbs can be naturally produced, i.e., by immunization of dromedaries, camels, llamas, alpacas or sharks (Ghahroudi et al., "Selection and Identification of Single Domain Antibody Fragments from Camel Heavy-Chain Antibodies," *FEBS Letters* 414(3): 521-526 (1997), which is hereby incorporated by reference in its entirety). Alternatively, the sDAb can be produced in microorganisms or derived from conventional whole antibodies (Harmsen et al., "Properties, Production, and Applications of Camelid Single-Domain Antibody Fragments," *Appl. Microbiol. Biotechnology* 77:13-22 (2007), Holt et al., "Domain Antibodies: Proteins for Therapy," *Trends Biotech.* 21(11): 484-490 (2003), which is hereby incorporated by reference in its entirety).

Fab (Fragment antigen binding) refers to the fragments of the antibody consisting of the VL, CL, VH, and CH1 domains. Those generated following papain digestion simply are referred to as Fab and do not retain the heavy chain hinge region. Following pepsin digestion, various Fabs retaining the heavy chain hinge are generated. Those fragments with the interchain disulfide bonds intact are referred to as F(ab')2, while a single Fab' results when the disulfide bonds are not retained. F(ab')$_2$ fragments have higher avidity for antigen that the monovalent Fab fragments.

Tribodies are multifunctional recombinant antibody derivatives that combine two scFv fragments with a Fab fragment. The Fab fragment serves as a specific heterodimerization signal, and the two scFv fragments are each fused to a different Fab chain (Schoonjans et al., "Efficient Heterodimerization of Recombinant Bi- and Trispecific Antibodies," *Bioseparation* 9(3): 179-183 (2000), which is hereby incorporated by reference in its entirety).

Diabodies are small bivalent and bispecific antibody fragments that comprise a heavy (VH) chain variable domain connected to a light chain variable domain (VL) on the same polypeptide chain (VH-VL) connected by a peptide linker that is too short to allow pairing between the two domains on the same chain (Hollinger et al., "'Diabodies': Small Bivalent and Bispecific Antibody Fragments," *Proc. Natl. Acad. Sci. U.S.A.* 90(14):6444-6448 (1993), which is hereby incorporated by reference in its entirety).

Methods for monoclonal antibody production are well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest. In one embodiment, monoclonal antibodies of the present invention are raised against the GPIIIa(49-66) peptide. The antibody-secreting lymphocytes are then fused with myeloma cells or transformed cells, thereby producing an immortal, immunoglobulin-secreting cell line (Milstein and Kohler, "Derivation of Specific Antibody-Producing Tissue Culture and Tumor Lines by Cell Fusion," *Eur. J. Immunol.* 6:511 (1976), which is hereby incorporated by reference in its entirety). The resulting fused cells, or hybridomas, are cultured, and screened for the production of the desired monoclonal antibodies. Colonies producing such antibodies are cloned, and grown either in vivo or in vitro to produce large quantities of antibody.

In another embodiment of the present invention, GPIIIa49-66 antibodies or antibody fragments can be isolated from antibody phage libraries generated using the techniques described in McCafferty et al., "Phage Antibodies: Filamentous Phage Displaying Antibody Variable Domains," *Nature* 348:552-554 (1990), which is hereby incorporated by reference in its entirety. Li et al., "Platelet Fragmentation Requires a Specific Structural Conformation of Human Monoclonal Antibody Against β3 Integrin," *J. Biol. Chem.* 283(6):3224-3230 (2008), which is hereby incorporated by reference in their entirety, describes the isolation of nine monoclonal human antibodies from a human scFv antibody library using phage surface display technology. These antibodies are each capable of binding to GPIIIa49-66, and are suitable for use in the methods of the present invention. Thus, this technology is a very viable alternative to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al., which is hereby incorporated by reference in its entirety. The polynucleotides encoding a monoclonal antibody are isolated from mature B-cells or hybridoma cells. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells.

The monoclonal antibody of the present invention can be a humanized antibody. Such antibodies are used therapeutically to reduce antigenicity and human anti-mouse antibody responses when administered to a human subject. A human antibody is an antibody produced by a human or an antibody having an amino acid sequence corresponding to an antibody produced by a human. An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," *Nature* 321: 522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). Humanized antibodies can be produced using various techniques known in the art. Immortalized human B lymphocytes immunized in vitro or isolated from an immunized individual that produce an antibody directed against a target antigen can be generated (See e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the humanized antibody can be selected from a phage library, where that phage library expresses human antibodies (Li et al., "Platelet Fragmentation Requires a Specific Structural Conformation of Human Monoclonal Antibody Against β3 Integrin," *J. Biol. Chem.* 283(6):3224-3230 (2008), Vaughan et al., "Human Antibodies with Sub-Nanomolar Affinities Isolated from a Large Non-immunized Phage Display Library," *Nature Biotechnology,* 14:309-314 (1996); Sheets et al., "Efficient Construction of a Large Nonimmune Phage Antibody Library: The Production of High-Affinity Human Single-Chain Antibodies to Protein Antigens," *Proc Nat'l Acad Sci U.S.A.* 95:6157-6162 (1998); Hoogenboom et al., "By-passing Immunisation. Human Antibodies From Synthetic Repertoires of Germline VH Gene Segments Rearranged In Vitro," *J Mol Biol* 227:381-8 (1992); Marks et al., "By-passing Immunization. Human Antibodies from V-gene Libraries Displayed on Phage," *J Mol Biol* 222:581-97 (1991), which are hereby incorporated by reference in their entirety). Humanized antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety Procedures for raising polyclonal antibodies are also well known. Typically, such antibodies can be raised by administering the peptide or polypeptide containing the epitope of interest subcutaneously to New Zealand white rabbits which have been bled to obtain pre-immune serum. In one embodiment of the present invention, polyclonal antibodies are raised against the GIIIa49-66 linear epitope having an amino acid sequence of SEQ ID NO: 1. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody modifications that enhance stability or facilitate delivery of the antibody are also encompassed by the present invention. For example, the antibody may be linked to one of a variety of nonproteinaceous polymers, e.g., polyethylene glycol, polypropylene glycol, polyoxyalkylenes, or copolymers of polyethylene glycol and polypropylene glycol.

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J Mol Biol* 284:1141-1151 (1998); Koide et al., "Probing Protein Conformational Changes in Living Cells by Using Designer Binding Proteins: Application to the Estrogen Receptor," *Proc Nat'l Acad Sci USA* 99:1253-1258 (2002), each of which is hereby incorporated by reference in its entirety); and those known as affibodies, which are derived from the stable alpha-helical bacterial receptor domain Z of *staphylococcal* protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

In accordance with the methods of the present invention, administering a GPIIIa49-66 targeting agent to a subject to inhibit metastasis or treat cancer can be done concurrently with other therapeutic approaches, i.e., the GPIIIa49-66 targeting agent is administered as part of a combination therapy. Accordingly, in one embodiment of the invention, the agent is administered in combination with one or more additional inhibitors of metastatic disease progression or cancer therapeutics, such as, a chemotherapeutic, radiation therapy (e.g., external beam radiation therapy or brachytherapy), an anti-angiogenic therapeutic, a premetastatic niche formation inhibitor, a stromal inhibitor, a bone-marrow derived cell inhibitor, a myeloid derived suppressor cell inhibitor, and extracellular matrix protein inhibitors.

Suitable chemotherapeutic agents for combination therapies include, without limitation, alkylating agents (e.g., chlorambucil, cyclophophamide, CCNU, melphalan, procarbazine, thiotepa, BCNU, and busulfan), antimetabolites (e.g., methotraxate, 6-mercaptopurine, and 5-fluorouracil), anthracyclines (e.g., daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Anti-angiogenic or anti-vasculogenic therapeutics suitable for use in combination with an GPIIIa49-66 targeting agent of the present invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art and are under clinical development (see e.g., Wu et al., "Anti-Angiogenic Therapeutic Drugs for the Treatment of Human Cancer," *J Cancer Molecules* 4(2):37-45 (2008) and Bissell et al., "Why Don't We Get More Cancer? A Proposed Role of the Microenvironment in Restraining Cancer Progression," *Nat. Med.* 17(3):320-329 (2011), which are hereby incorporated by reference in their entirety). These angiogenic inhibitors include, without limitation, Endostatin (an endothelial cell proliferation and angiogenesis inhibitors), Gefitinib (an ErbB inhibitor), Lapatinib (a dual ErbB1/ErbB2 inhibitor), Erlotinib (HER1/EGFR inhibitor), Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR, Kit, Flt3, Tet and CSF1R), Sorafenib (multi-targeted inhibit of VEGFR and PDGFR), Pazopanib (a multi-targeted inhibitor of VEGFR-1, VEGFR-2, VEGFR-3, PDGF-$\alpha$, PDGFR-$\beta$, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $\alpha_v\beta_3$ antibody).

Suitable stromal inhibitors for use in the present invention are known in the art (see Bissell et al., "Why Don't We Get More Cancer? A Proposed Role of the Microenvironment in Restraining Cancer Progression," *Nat. Med.* 17(3):320-329 (2011), which is hereby incorporated by reference in its entirety) and include, without limitation, MK-2461 (a small molecule inhibit of c-MET kinase), Anastrazole (an aromatase inhibitor), AMD070 (a CXCR4 inhibitor), IPI-926 (a hedgehog pathway inhibitor), AVE1642 (a humanized monoclonal antibody targeting insulin-like growth factor-1 receptor), BGJ398 (a small molecule inhibitor of fibroblast growth factor receptors), Celecoxib (a COX-2 inhibitor), MK0822 (a cathepsin K inhibitor), Bortezomib (a 26S proteasome complex inhibitor), Zoledronate (a small-molecule pyrophosphate analog that inhibits the differentiation of myeloid cells and affects tumor-associated macrophages), Denosumab (a human monoclonal antibody the binds RANKL), and PG545, a heparan sulfate mimetic that inhibits heparanase activity.

Suitable premetastatic niche formation inhibitors include, without limitation, bone-marrow derived cell inhibitors (e.g., VEGFR1 inhibitor or CD11b inhibitor), S100a8 inhibitor, S100a9 inhibitors, Lysyl oxidase inhibitor, matrix metalloproteinase-9 and -2 inhibitors (e.g., Incyclinide, PCK3145).

Suitable extracellular matrix protein inhibitors include, without limitation, DX2400, an MMP-14 inhibitor, and PEGPH20, a covalently modified form of hyaluronidase which catalyzes the degradation of the extracellular matrix component hyalurona.

In another embodiment of the present invention, the GPIIIa49-66 targeting agent is administered as a part of an adjuvant therapy regime. In particular, this involves chemotherapy, hormone therapy, radiation therapy, immunotherapy, or a targeted therapy together with an GPIIIa49-66 targeting agent prior to and/or after surgery. In addition, the present invention may be used to treat patients after primary surgery who may not otherwise receive treatment, i.e. those patients with primary complete resection without evidence of residual or distant disease in order to prevent metastatic cell spread and disease formation.

In practicing the methods of the present invention, the administering step is carried out to achieve inhibition of metastatic cell spread, metastatic disease progression, or primary tumor growth. As will be apparent to one of ordinary skill in the art, administering any of the agents of the present invention may be carried out systemically or via direct or local administration to the tumor site using generally known methods. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. Therapeutic agents of the invention may be administered alone or with suitable pharmaceutical carriers, and can be in solid or liquid form such as, tablets, capsules, powders, solutions, suspensions, or emulsions.

The agents of the present invention may be orally administered, for example, with an inert diluent, with an assimilable edible carrier, enclosed in hard or soft shell capsules, compressed into tablets, or incorporated directly with the food of the diet. Such compositions and preparations should contain at least 0.1% of active compound. The percentage of the agent in these compositions may, of course, be varied and may conveniently be between about 2% to about 60% of the weight of the unit. The amount of active agent in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The GPIIIa49-66 targeting agent of the present invention may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents of the present invention may also be administered directly to the airways in the form of an aerosol. For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Effective doses of the compositions of the present invention, for the treatment of a primary tumor or tumor metastasis vary depending upon many different factors, including type and stage of cancer, means of administration, target site, physiological state of the patient, other medications or therapies administered, and physical state of the patient relative to other medical complications. Treatment dosages need to be titrated to optimize safety and efficacy.

EXAMPLES

The examples below are intended to exemplify the practice of the present invention but are by no means intended to limit the scope thereof.

Materials and Methods for Examples 1-9

Cell lines. Lewis lung carcinoma cells (LLCs), Human umbilical vein endothelial cells (HUVECs), and B16 melanoma cells (B16) were all purchased from American Type Culture Collection (Rockville, Md.). LLC and B16 cells were maintained in RPMI 1640 medium (Gibco, Grand Island, N.Y.) supplemented with 10% newborn calf serum (Gibco). HUVECs were cultured in iscove's modified Dulbecco's medium (Gibco) containing 10% (v/v) fetal bovine serum (Gibco) and supplemented with 90 μg/mL heparin sodium (Sigma, St. Louis, Mo.), 2 ng/mL basic fibroblast growth factor (R&D Systems, Minneapolis, Minn.). All culture systems were incubated at 37° C. in a humidified, 5% $CO_2$ atmosphere.

Antibodies. Human monoclonal scFv Ab against GPIIIa49-66 (A11) and control scFv Ab (13CG2) were prepared as described (Li et al., "Platelet Fragmentation Requires a Specific Structural Conformation of Human Monoclonal Antibody Against beta3 Integrin," *J. Biol. Chem.* 283(6):3224-3230 (2008); Dang et al., "A Humanized Single-Chain Variable Fragment Antibody Against beta3 Integrin in *Escherichia coli,*" *Hybridoma* 30(6):543-548 (2011), which are hereby incorporated by reference in their entirety).

Mice. C57BL/6J background mice used in the following experiments were raised under specific pathogen-free conditions. All procedures in animal experiments were approved by the Institutional Animal Care and Use Committee of East China Normal University.

Monocyte isolation and assay of platelet adhesion to monocytes. The monocytes were isolated from human blood samples by the adherence technique (de Almeida et al., "A Simple Method for Human Peripheral Monocyte Isolation," *Mem. Inst. Oswaldo Cruz.* 95(2):221-223 (2000), which is hereby incorporated by reference in its entirety). RPMI 1640 containing 10% FCS and heparin (10-15 IU/mL) was added to the blood sample in 1:1 ratio (v/v) in a Petri dish and kept at 37° C. in an incubator with 5% $CO_2$. After 2 hours of incubation, the medium was decanted out and the Petri dish was rinsed four times with heparin/PBS solution (containing per liter: NaCl, 8 g; KCl, 0.2 g; $Na_2HPO_4$, 1.15 g; $KH_2PO_4$, 0.2 g and heparin, 10 IU/mL; pH 7.2). The attached monocytes, devoid of red blood cells, were detached from Petri dish using a rubber policeman, centrifuged and resuspended in RPMI 1640 in a final concentration of $2 \times 10^6$ monocyte/μL. The monocyte suspension, kept at 37° C. and was used within 24 hours after preparation.

The platelet-monocytes adhesion assay was performed as previously published (Larsen et al., "PADGEM-Dependent Adhesion of Platelets to Monocytes and Neutrophlis is Mediated by Lineage-Specific Carbohydrate, LNF III (CD 15)," *Cell* 63(3):467-474 (1990), which is hereby incorporated by reference in its entirety). Briefly, platelets were activated by incubating cells without stirring for 20 minutes at 22° C. with thrombin (0.25 U/mL), followed by incubation with various concentrations of A11 for 4 hours at 37° C. Twenty microliter of treated platelet suspension ($2 \times 10^8$/mL) was mixed with an equal volume of the monocyte suspension ($2 \times 10^6$/mL) and incubated for 30 minutes at room temperature in a microtube. An aliquot of the cell suspension was then placed in a Neubauer chamber and evaluated by light microscopy. Three samples from each assay were evaluated by counting 200 monocytes and scoring the percentage of the cells with various numbers of platelets attached to them: monocytes with less than 5, between 5 to 10, and more than 10 attached platelets.

Fluorescence labeling of tumor cells. Tumor cells were incubated with fluorescent dye DIO (Beyotime Institute of Biotechnology, China) (5 µg/mL) for 30 minutes at 37° C. After washing three times with PBS, the pellet was resuspended in RPMI 1640 medium for later use.

Establishment of hypoxia-reoxygenation model. The cells were cultured in a 37° C., 95% air and 5% $CO_2$ incubator to 90% confluence, and then the culture flasks or plates were transferred into an air-tight container infused with a mixture air of 95% $N_2$ and 5% $CO_2$ for 24 hours at 37° C. followed by culturing at 37° C., 95% air and 5% $CO_2$ incubator for 2 hours.

Disaggregation and destruction of ex vivo tumor-platelet aggregates. Disaggregation and destruction of ex vivo tumor-platelet aggregates were determined as previously published (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010), which is hereby incorporated by reference in its entirety). To create tumor-platelet aggregates, thrombin (0.25 U/mL) was incubated with a tumor cell—platelet mixture (platelet: tumor=3,000:1) for 1 hour at 37° C. with intermittent shaking, followed by gravity sedimentation at room temperature for 30 minutes. Excess reagents were removed by washing in PBS. A total of 0.5 µM A11 or control scFv (13CG2) was added at different time intervals, and the remaining tumor-platelet/aggregate was emmerated as previously described (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010), which is hereby incorporated by reference in its entirety).

Assay of tumor cells adhesion to activated platelets. The adhesion of tumor cells to activated platelets was measured as previously described with slight modifications (Karpatkin et al., "Lack of Effect of In Vivo Prostacyclin on the Development of Pulmonary Metastases in Mice Following Intravenous Injection of CT26 Colon Carcinoma, Lewis Lung Carcinoma, or B16 Amelanotic Melanoma Cells," *Cancer Res.* 44(9):3880-3883 (1984), which is hereby incorporated by reference in its entirety). Briefly, thrombin (0.25 U/mL) activated platelets were incubated in 96-well flat bottomed microtitre plates at a density of $3 \times 10^7$ cells/well, and then treated with various concentrations of A11 for 4 hours at 37° C. Plates were then blocked with 0.01M PBS plus 1% BSA for 1 hour at 37° C., and washed three times with PBS-BSA plus 0.9 mM $CaCl_2$, 0.9 mM $MgCl_2$ before the addition of $1 \times 10^4$ DIO-labeled tumor cells for a 4 hours co-incubation. The non-adherent tumor cells were discarded. The fluorescent intensity of adherent tumor cells was observed with a fluorescence plate reader (Molecular Devices Corporation, USA).

Assay of activated platelets adhesion to endothelial cells. For the platelet-endothelial adhesion assay, HUVECs were incubated in 96-well flat bottomed microtitre plates at a density of $1 \times 10^4$ cells/well until the cellular confluence reached 90%. The treatment of hypoxia reoxygenation was applied as described above. After labeling platelets with sulfo-NHS-LC-Biotin (PIERCE, USA) as described previously (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010), which is hereby incorporated by reference in its entirety), labeled platelets were activated by thrombin, and then added into the HUVEC culture plate, followed by co-incubation at 37° C. for 4 hours in the presence of various concentrations of A11 or control scFv (13CG2) (platelet: HUVECs=1,000:1). The non-adherent platelets were aspirated off before the addition of horseradish peroxidase-conjugated streptavidin to be developed with the TMB substrate. The extent of adhesion at each concentration of A11 was detected by comparison with the standard curve and expressed as the percentage of the control where the platelets were not preincubated with A11.

Assay of tumor cells adhesion to endothelial cells. HUVECs were incubated in 96-well flat bottomed microtitre plates at a density of $1 \times 10^4$ cells/well until the cellular confluence reached 90%. The treatment of hypoxia-reoxygenation was applied as described above. Platelets were activated by thrombin (0.25 U/mL), and then co-incubated with the HUVEC culture plate at 37° C. for 4 hours in the presence of A11 or control scFv 13CG2 (platelet: HUVECs=1,000:1). The non-adherent platelets were aspirated off before the addition of Dio-labeled B16 melanoma cells. The adhesion status of B16 melanoma cells with HUVECs was detected under a fluorescence microscope.

MTT assay. The effects of A11 on the growth of HUVEC, LLC, and B16 cells were assessed using the MTT assay. In brief, HUVEC, B16, or LLC cells were evenly distributed per well and grown in 96-well plates for 24 hours. The cells were treated with various concentrations of A11, ranged from 0.1 to 1000 µg/mL, and incubated for 7 days. At the termination of the incubation, 20 µL MTT (3-[4,5-dimethylthiazol-2-yl]-2,5-diphenyl-tetrazolium bromide; Beyotime, China) was added to each well and incubated at 37° C., with 5% $CO_2$ for 4 hours. After removing the supernatant, 150 µL DMSO was added into each well and the plate was agitated gently at room temperature for 10 minutes. The optical density at 562 nm was determined using a 96-well plate reader. Each experiment was repeated three times. The percentage of cell growth inhibition was calculated as follows: Cell growth rate (%)=A562 (A11)/A562 (control) *100%.

Transwell migration assay. Transwell plates (Costar 3422, Corning, Lowell, Mass., USA) were used to measure HUVEC or tumor cell chemotaxis. HUVECs or tumor cells were grown to 75% confluence in 10% bovine serum albumin (BSA)-DEME culture media for 24 hours, followed by 0.1% BSA-DMEM for an additional 4 or 24 hours, respectively. Cells were trypsinized, washed with PBS, resuspended in 0.1% BSA-DMEM, and 200 µL ($5 \times 10^4$ cells) were incubated with various concentrations of A11 at 37° C. for 1 hour, and then added to the upper chamber. The lower chamber contained 600 µL 0.1% BSA-DMEM. Plates were incubated at 37° C. 5% $CO_2$ atmosphere for 24 hours. Inserts was removed, washed with PBS, and then stained with crystal violet for 10 minutes. Cells and solution were removed from the bottom of the insert. Excess stain was removed from the bottom of the insert by swabbing with a cotton-tipped applicator and then allowed to dry. Destaining was performed in 10% acetic acid for 10 minutes. The solution was then transferred to a 96-well plate and the absorbance read at 595 nm. Percentage inhibition of migrated cells was expressed on the basis of untreated cells (control) representing 100%.

Matrigel angiogenesis assay in vitro (tube formation). HUVECs were cultured in complete EGM-2 media before being plated in 96-well plates ($2 \times 10^4$ cells/well) previously coated with 50 µL of growth factor—reduced Basement Membrane Extract (BME) (Trevigen, Gaithersburg, Md., USA), in the presence of A11, control scFv (13CG2), or control inhibitor (Sulforaphane). HUVECs start to form tubes at 4 hours. Tube formation is optimal after 10 hours and begins to fade after 16 hours. The morphology of capillary-like structures formed by HUVEC 10 hours after culturing was visualized using an inverted microscope and photographed with a digital camera (×40). The degree of tube formation was quantified by measuring the area occupied by the tube in five random fields from each well with an imaging system (Image-Pro).

In vivo Matrigel plug assay. Matrigel plug assay was performed as described previously (Drabkin et al., "Spectrophotometric Constants for Common Hemoglobin Derivatives in Human, Dog, and Rabbit Blood," *J. Biol. Chem.* 98:719-733 (1932), which is hereby incorporated by reference in its entirety). Briefly, C57BL/6 mice were injected s.c. with 0.5 mL of Matrigel (BD Biosciences, San Jose, Calif., USA) containing 50 µg A11, 100 ng VEGF, and 10 units heparin. The injected Matrigel rapidly formed a single, solid gel plug. After 7 days, the skin of the mouse was easily pulled back to expose the Matrigel plug, which remained intact. Hemoglobin (Hb) content in the Matrigel plugs was measured using the Drabkin reagent (Sigma, St. Louis, Mo., USA) for quantification of blood vessel formation. The concentration of Hb was calculated from a known amount of Hb assayed in parallel.

Detection of the effect of platelets on metastasis of B16 tumor cells in vivo. Platelets were isolated from healthy C57BL/6J mice as described previously (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010), which is hereby incorporated by reference in its entirety). Then B16 cells were coincubated with isolated platelets for 30 minutes (platelet: tumor cell ratio=1000:1). C57BL/6J mice were randomly divided into two groups, and were injected with B16 cells ($2 \times 10^5$/mouse) or platelet-incubated B16 cells via the tail vein, respectively. After 3 weeks, the mice were sacrificed and the surface metastatic nodules on the lungs were counted.

Determination of Mouse Platelet Count. Platelet counts were done as described previously (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010), which is hereby incorporated by reference in its entirety). Briefly a total of 20 µL of blood was drawn into Unopettes (No. 365855, Becton Dickson) that contained an optimal anticoagulant concentration and diluent for quantitating platelet counts by phase-contrast microscopy.

Bleeding Time. To determine the bleeding time, the mouse tail vein was severed 2 mm from its tip and blotted every 30 seconds on a circular sheet of filter paper to obtain an objective measurement. Termination of the bleeding time was recorded after absence of blood on the filter paper. Bleeding time differences were recorded by an unbiased observer and confirmed by two other observers, blinded to the experimental status of the mice.

Spontaneous lung metastasis assay. For spontaneous metastasis (which measures metastasis from a primary tumor), 6-week-old C57BL/6J female mice were subcutaneously injected with $2.5 \times 10^5$ viable LLC tumor cells. The primary tumor was resected 10 days later, and mice were treated with A11 or control scFv Ab (13CG2), and three times per week thereafter. After 3 weeks, the mice were sacrificed, and the surface metastatic nodules on the lungs were counted. The volume of each nodule was calculated from its diameter (d), by assuming the nodules are spheres. Nodule volumes were calculated by the following formula: volume (mm$^3$)=$\pi/6 \times d^3$ (Karpatkin et al., "Lack of Effect of In Vivo Prostacyclin on the Development of Pulmonary Metastases in Mice Following Intravenous Injection of CT26 Colon Carcinoma, Lewis Lung Carcinoma, or B16 Amelanotic Melanoma Cells," *Cancer Res.* 44(9):3880-3883 (1984), which is hereby incorporated by reference in its entirety). The mean nodule volume for each mouse was calculated by dividing the total pulmonary nodule volume for each group of mice by the number of mice in each group.

Experimental lung metastasis assay. Experimental metastasis refers to the later steps of the metastatic migration process (extravasation from the blood stream and then growth into pulmonary tumor). In the LLC model, 6-week-old C57BL/6J female mice were randomly divided into five groups: Group 1: mice intravenously pretreated with A11 (25 µg/mice) 12 hours prior to i.v. injection of LLC tumor cells ($2.5 \times 10^5$/mouse); Group 2: mice were pretreated with A11 4 hours prior to injection of tumor cells; Group 3: mice were first given injections of tumor cells and then simultaneously treated with A11; Group 4: mice were first given injections of tumor cells and then treated with A11 4 hours later; Group 5: mice were treated with A11 12 hours after injection of tumor cells. These mice were then given injections of A11 at 24 hours, and three times per week thereafter. Suitable controls were given injections of control scFv 13CG2. In the B16 melanoma model, mice first received an i.v. injection of B16 tumor cells ($2 \times 10^5$/mouse) and then were treated with A11 at 0 and 24 hours post tumor inoculation, followed by three treatments per week thereafter. In a control group, mice received both A11 and an equal molar quantity of GPIIIa49-66 albumin conjugate. After 3 weeks, the mice were sacrificed to harvest the lungs. The mean number of surface nodules per lung and mean volume of nodules per lung were determined as described above.

Assay of tumor growth. Six-week-old C57BL/6J mice were subcutaneously (s.c.) implanted with $5 \times 10^5$ LLC tumor cells. When tumors became easily palpable, mice were randomly divided into two groups. A11 (25 µg/mice) was injected i.v. into mice thrice per week for 2 successive weeks, whereas the controls received injection of saline. Tumor dimensions were measured with calipers for calculation of tumor volume.

Assay of early invasion of B16 melanoma in lung tissue. The C57BL/6J mice were randomly divided into two groups, and then treated with A11 or control scFv Ab (13CG2) after i.v. injection of DIO labeled B16 cells. Six hours later, the mice were sacrificed. The lung tissue was collected at the maximal longitudinal cut surface across the hilus pulmonis and prepared into frozen slices. The adhesion of B16 to vessels was observed under a fluorescence microscope.

Statistical analysis. P values were determined through the two-tailed Student's t test. Differences were considered statistically significant when $p<0.05$.

Example 1

Platelets Promote Pulmonary Metastasis in the B16 Tumor Model

Extensive experimental evidence and clinical studies suggested platelets play an important role during the early phase of tumor metastasis (Troxler et al., "Platelet Function and Antiplatelet Therapy," *Br. J. Surg.* 94(6):674-682 (2007); Rothwell et al., "Effect of Daily Aspirin on Risk of Cancer Metastasis: A Study of Incident Cancers During Randomized Controlled Trials," *Lancet* 379(9826):1591-1601 (2012); Sierko et al., "Inhibition of Platelet Function: Does it Offer a Chance of Better Cancer Progression Control?"

Semin. Thromb. Hemost. 33(7):712-721 (2007); Trikha et al., "Role of AlphaII(b)beta3 Integrin in Prostate Cancer Metastasis," *Prostate* 35(3):185-192 (1998), which are hereby incorporated by reference in their entirety). FIG. 1A shows the events occurring following tumor intravasation, tumor platelet-endothelial cell binding, platelet-tumor thrombus formation, tumor-platelet embolization, angiogenesis, and extravasation. Platelet promotion of the experimental metastasis of B16 melanoma was confirmed in vivo. As noted in FIG. 1B, B16 melanoma cells co-incubated with platelets had a markedly increased number of surface pulmonary nodules compared to B16 melanoma cells alone (16±3.2 vs 5±1.3, **p<0.001). In lung tissue H-E slides, the number of metastatic tumors also increased markedly in comparison to the platelet free control group. It has previously been demonstrated that humanized anti-platelet GPIIIa49-66 scFv Ab (A11) preferentially fragments activated versus resting platelets (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010); Dang et al., "A Humanized Single-Chain Variable Fragment Antibody Against beta3 Integrin in *Escherichia coli*," *Hybridoma* 30(6):543-548 (2011), which are hereby incorporated by reference in their entirety). It was hypothesized that A11 may inhibit tumor metastasis by preferentially fragmenting activated platelets in the tumor microenvironment (FIG. 1C).

Example 2

Effect of A11 on Spontaneous Metastasis of Lewis Lung Carcinoma (LLC)

The effect of A11 on spontaneous lung metastases of LLCs was examined first. FIG. 2A shows the treatment protocol. FIG. 2B demonstrates that the mean number of surface nodules per lung was significantly decreased in the A11 group compared to the control scFv 13CG2 (6.5±2.8 vs 18±4.3, *p<0.01). The mean volume of nodules per lung was reduced in the A11 group compared to the control (1.47±0.35 vs 3.45±0.64, *p<0.01) (FIG. 2C). Microscopic evaluation of lung tissues gave results that correlated with the macroscopic findings, i.e., the number of microscopic metastatic focuses was lower in the A11 group than in the control (FIG. 2D).

Example 3

Effect of A11 on Experimental Metastasis of LLC

Figure 3A:
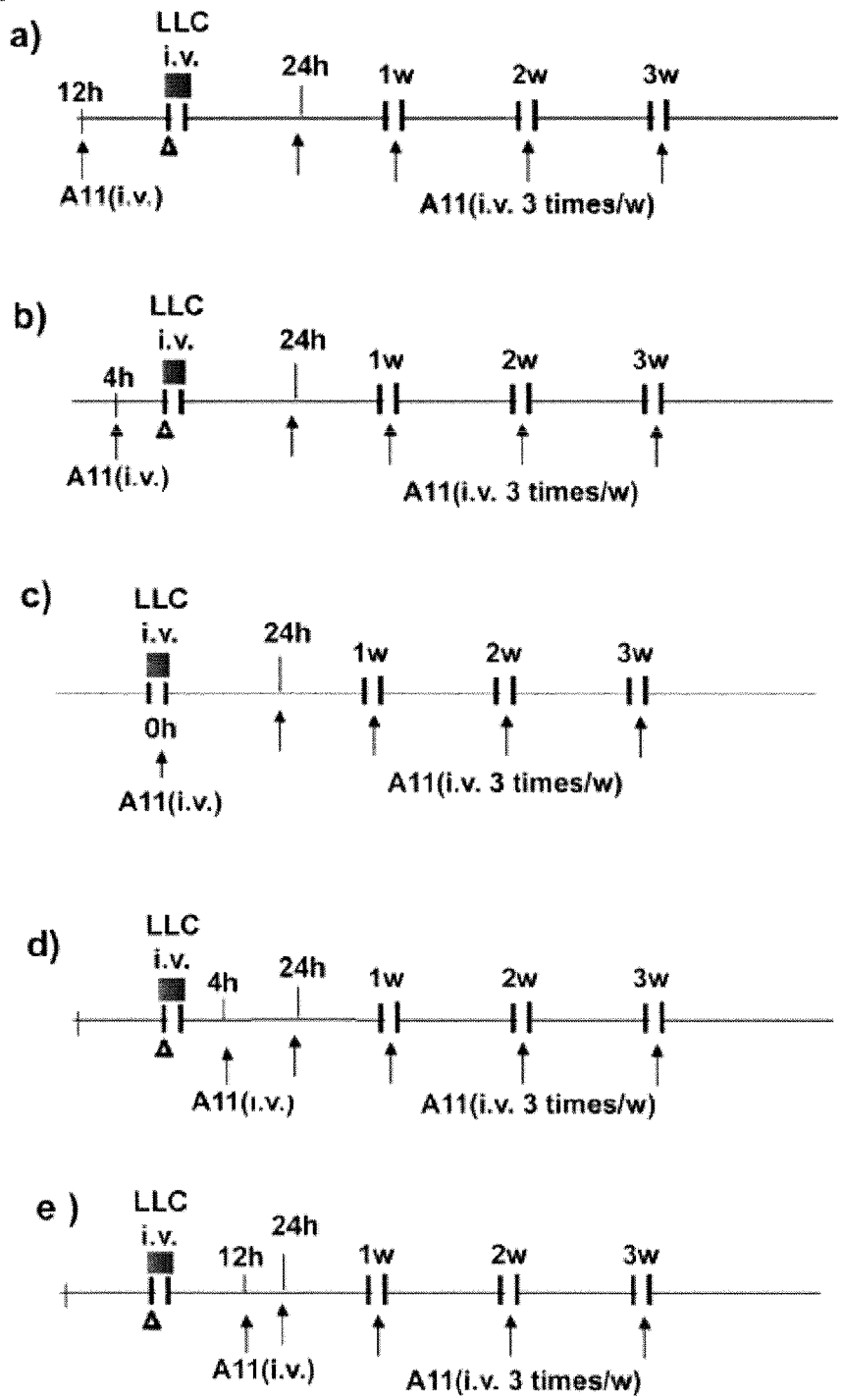
FIGS. 3A-3C depict the effect of A11 antibody treatment on experimental metastasis of LLC.
Figures 3B, 3C:
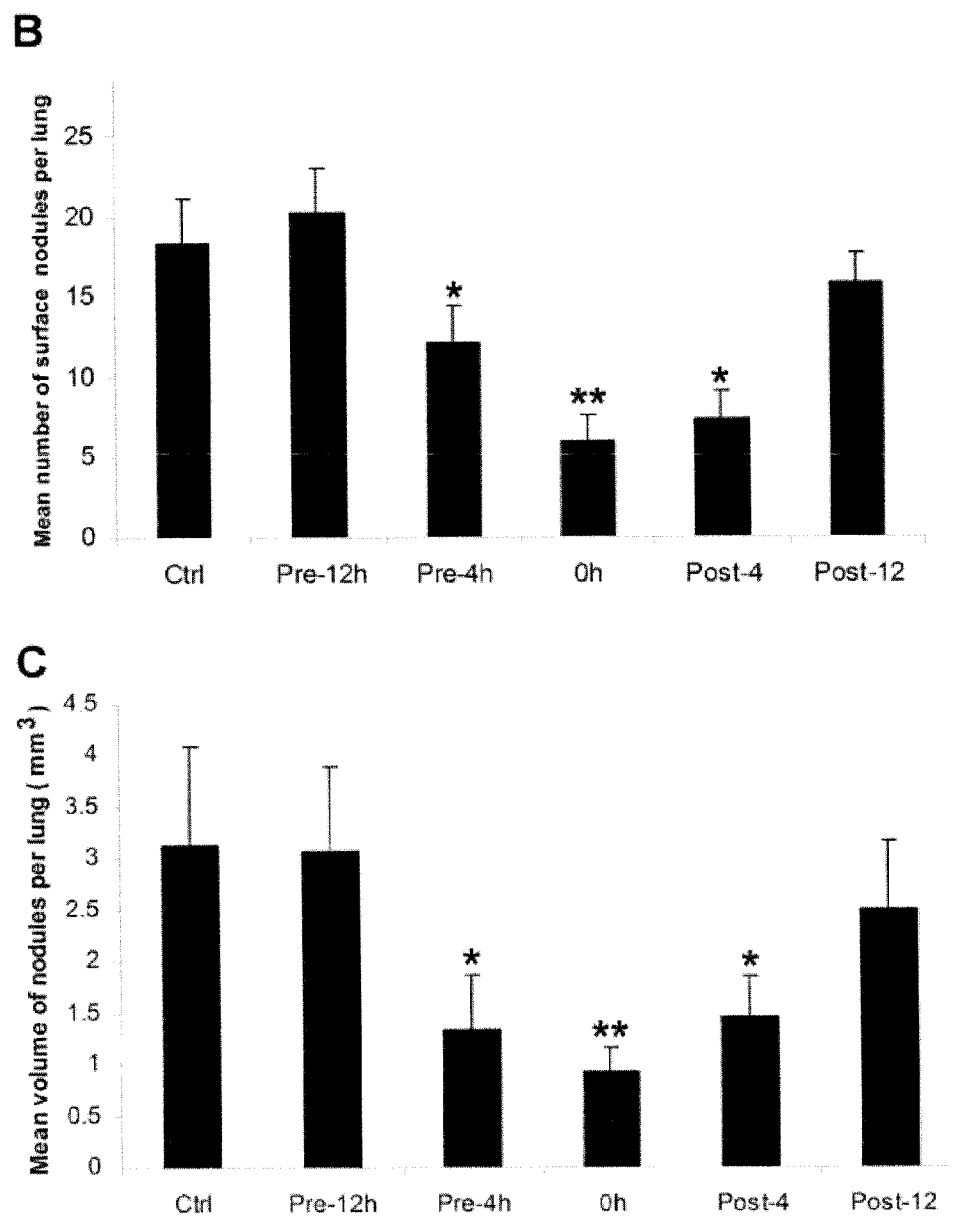

The effect of A11 on experimental lung metastases of LLC cells inoculated via the tail vein was evaluated. FIG. 3A shows five different pre-treated (a-b) or treated (c-e) protocols. FIG. 3B demonstrates that A11 immediate injection (0 h) after i.v. injection of LLC provided the best anti-metastatic effect. The mean number of surface nodules per lung was significantly decreased in the A11 group compared to the control scFv 13CG2 (5.9±1.7 vs 18.3±2.9, **p<0.001). A11 4 hours prior- or post-injection of LLCs also inhibits the mean number of surface nodules per lung [A11 (Pre-4 h) vs Ctrl, 12.1±2.3 vs 18.3±2.9; A11 (Post-4 h) vs Ctrl, 7.4±1.8 vs 18.3±2.9; *p<0.01]. No effect was noted on the inhibitory of the mean number of surface nodules per lung if A11 was given 12 hours prior- or post-injection of LLCs [A11 (Pre-12 h) vs Ctrl, 20.3±2.7 vs 18.3±2.9, p=0.17; A11 (Post-12 h) vs Ctrl, 15.8±1.9 vs 18.3±2.9; p=0.06]. A similar effect was noted in the mean volume of nodules per lung [A11 (0 h) vs Ctrl, 0.9±0.2 vs 3.1±0.9, **p<0.001; A11 (Pre-4 h) vs Ctrl, 1.3±0.5 vs 3.1±0.9; A11 (Post-4 h) vs Ctrl, 1.5±0.4 vs 3.1±0.9; *p<0.01; A11 (Pre-12 h) vs Ctrl, 3.1±0.8 vs 3.1±0.9, p=0.88; A11 (Post-12 h) vs Ctrl, 2.5±1.9 vs 3.1±0.7; p=0.15)] (FIG. 3B).

Example 4

Figure 4A:
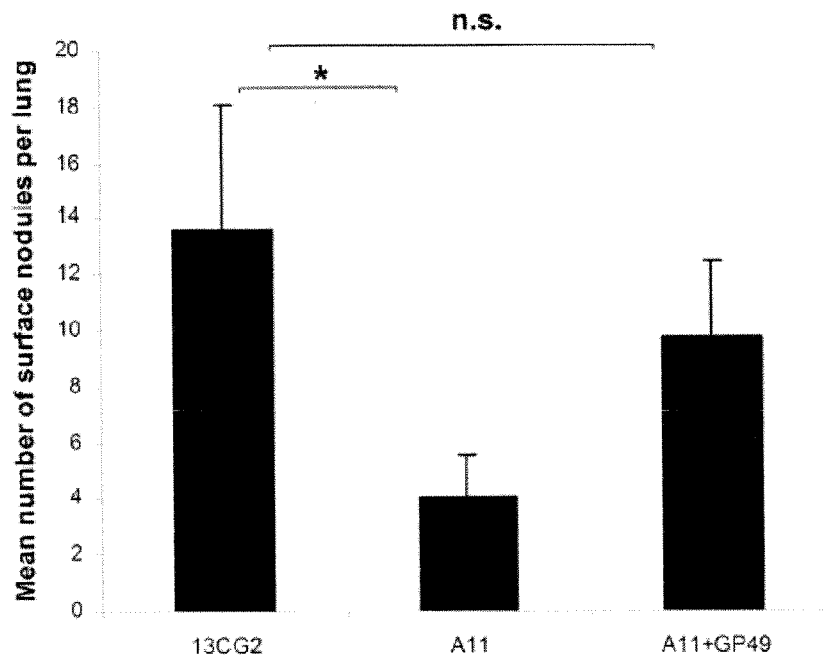
FIGS. 4A-4C demonstrate the pathophysiologic relevance of the platelet GPIIIa49-66 epitope (GP49) on experimental lung metastases of B16 melanoma. Mice were treated as described in the Example section. At day 21, mice were sacrificed.
Figure 4B:
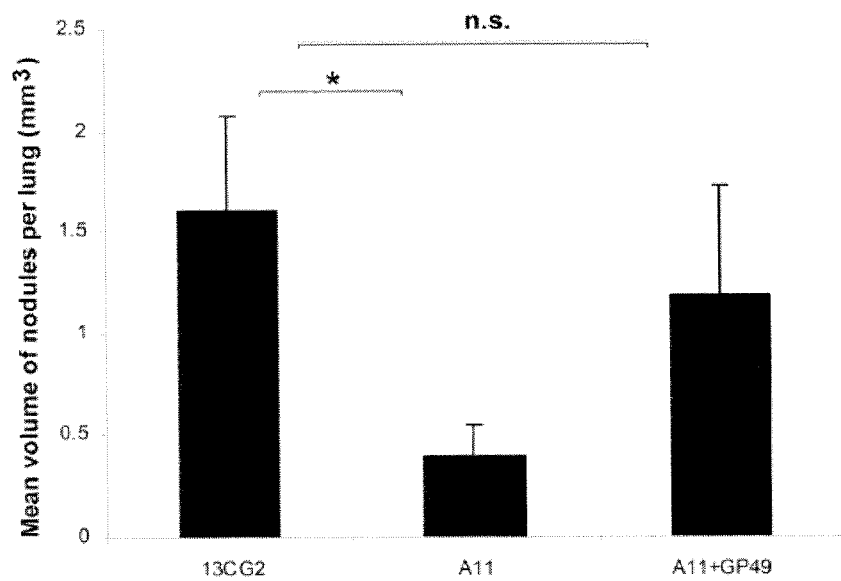
Figure 4C:
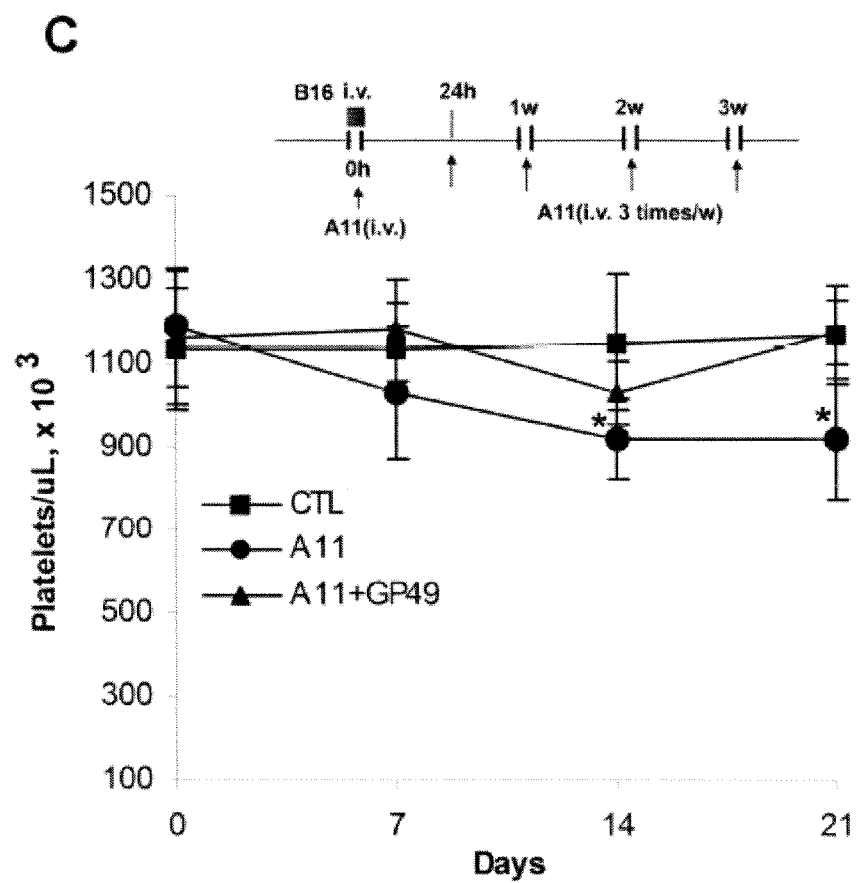

Pathophysiologic Relevance of Platelet GPIIIa49-66 Epitope (GP49) on Lung Metastases To prove the pathophysiologic relevance of the platelet GPIIIa49-66 epitope (GP49) on lung metastases, the effect of a GPIIIa49-66 albumin conjugate on blocking the A11 triggered anti-metastatic function was examined in experimental metastasis of B16 melanoma. It was postulated that a GPIIIa49-66 albumin conjugate would prevent the protective effect of A11 on pulmonary metastasis. This proved to be the case. FIG. 4A clearly demonstrates that A11 significantly decreased the mean number of surface nodules per lung in comparison with control scFv (13CG2) (A11 vs 13CG2, 4.0±1.5 vs 13.6±4.5, *p<0.001); however, injection of A11 with the simultaneous injection of equal molar quantities of GPIIIa49-66 albumin conjugate prevents the protective effect of A11 on pulmonary metastasis (A11+GP49 vs 13CG2, 9.8±2.7 vs 13.6±4.5, p>0.05). The same effect was noted on the mean volume of nodules per lung (A11 vs 13CG2, 0.4±0.15 vs 1.6±0.5, *p<0.001; A11+GP49 vs 13CG2, 1.1±0.4 vs 1.6±0.5, p>0.05) (FIG. 4B). FIG. 4C demonstrates the prevention of a platelet count drop induced by A11 in animals simultaneously treated with GPIIIa49-66 albumin conjugate.

Example 5

Effect of A11 on Early Invasion of Tumor Cells In Vivo

Figures 5A, 5B:
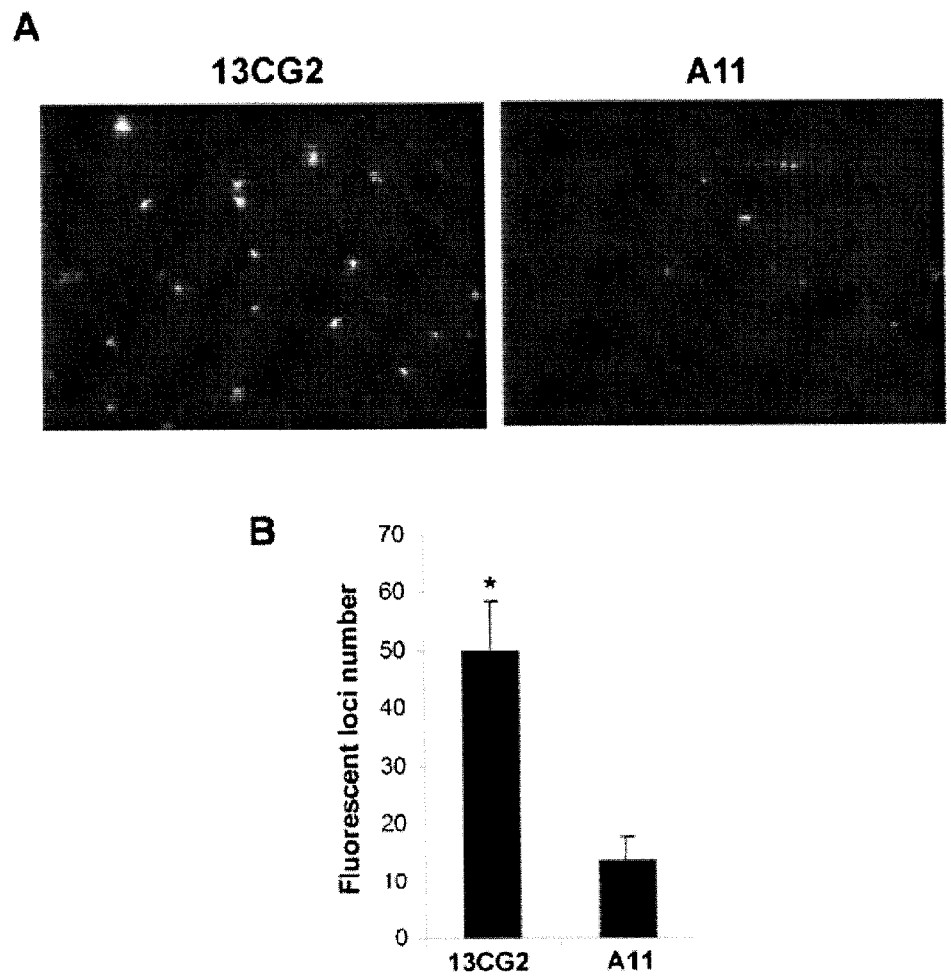
FIGS. 5A-5B show the effect of A11 on early invasion of B16 melanoma cells in lung tissue.

Since A11 is more effective in the time window from 4 hours prior- to 4 hours post-injection of tumor cells, it was reasoned that A11 may block the early invasion of tumor cells in vivo. Mice were treated with 13CG2 or A11 after i.v. injection of Dio-labeled B16 melanoma cells. Six hours later, the lungs were perfused and then used for frozen sections. The accumulation of B16 melanoma cells in lung tissue was observed. FIG. 5A demonstrates treatment with A11 results in a significant decrease of lung fluorescent loci in comparison with the 13CG2 control. The number of fluorescent loci associated with A11 was lower than 13CG2 control (49.8±8.6 vs 13.6±4.0, p<0.01) (FIG. 5B).

Example 6

Molecular Mechanisms by which A11 Inhibits Tumor Metastasis

Figure 6A:
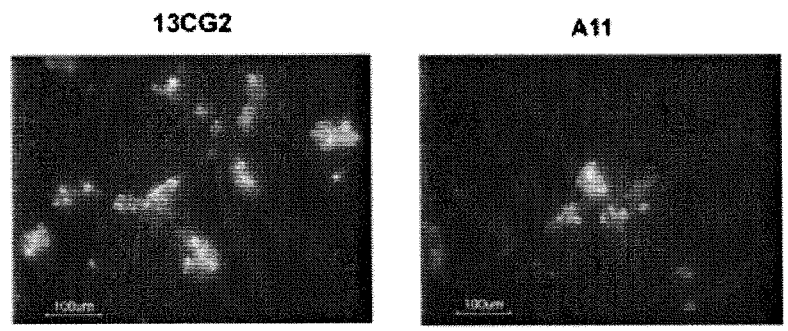
FIGS. 6A-6F depict the molecular mechanisms by which A11 inhibits tumor metastasis.
Figure 6B:
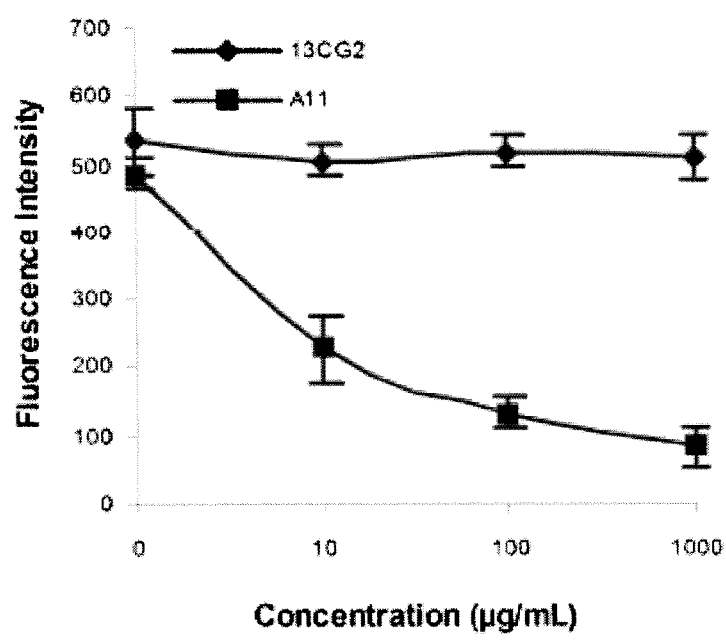
Figure 6C:
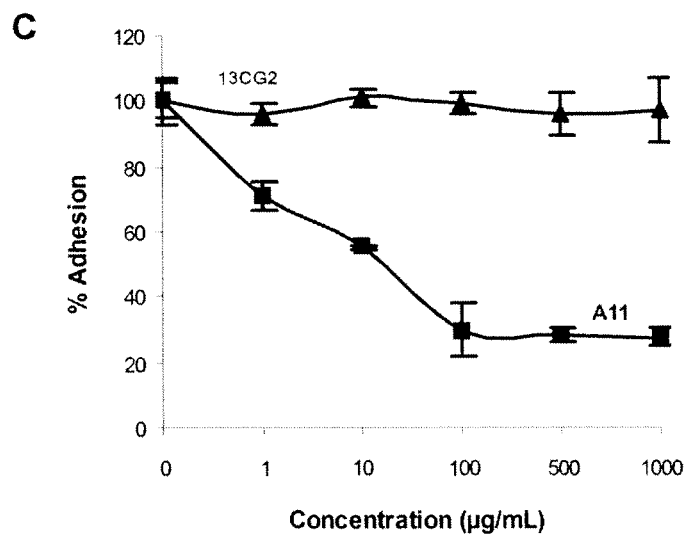

The effect of A11 on the interaction between activated platelets and tumor cells was investigated. FIG. 6A demonstrates the LLCs adhesion to activated platelet was significantly decreased when activated platelets were pretreated with A11. Note the approximately 82% fluorescence intensity reduction at the maximum A11 concentration, corresponding to reduced LLCs adhesion to activated platelets (FIG. 6B). A similar result was obtained using B16 melanoma cells. Since platelets mediated tumor cell adhesion to endothelial cells, it was reasoned that the adherence between platelets and endothelial cells will also be impaired by A11. FIG. 6C demonstrates that A11 reduced activated platelets adhesion to hypoxic-treated HUVECs in a dose-dependent manner with a maximum 71% inhibition. As expected the irrelevant control, scFv 13CG2, had no effect.

Figure 6D:
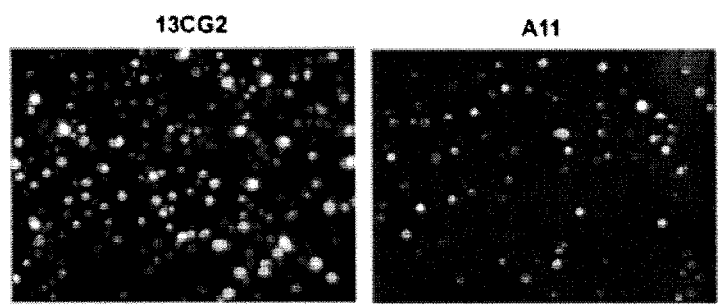
Figure 6E:
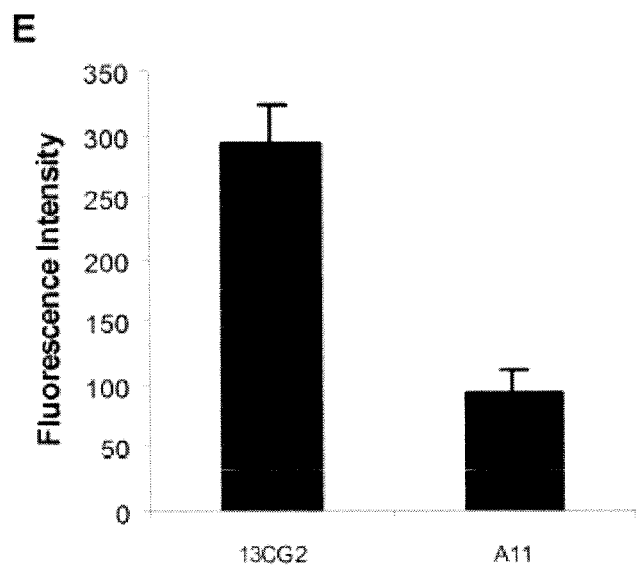

The effect of A11 on platelet mediated tumor cell adhesion to endothelial cells in vitro was examined. Hypoxic-treated HUVECs were coated on wells, and then incubated with 13CG2- or A11-treated activated platelets, respectively, followed by addition of Dio-labeled B16 melanoma cells. The adhesion status of B16 melanoma cells with HUVECs was detected using a fluorescence microscope (FIG. 6D). FIG. 6E demonstrates that the fluorescence intensity, corresponding to B16 melanoma cell adhesion to HUVECs, significantly decreased when activated platelets were treated with A11 (291.25±31.98 vs 95±17.79, p<0.05).

Figure 6F:
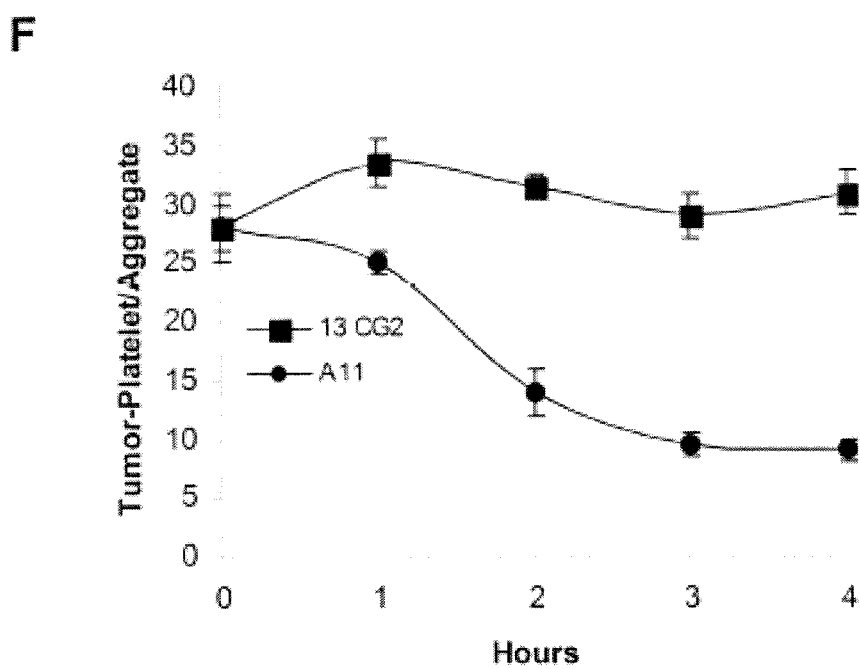
Figure 7:
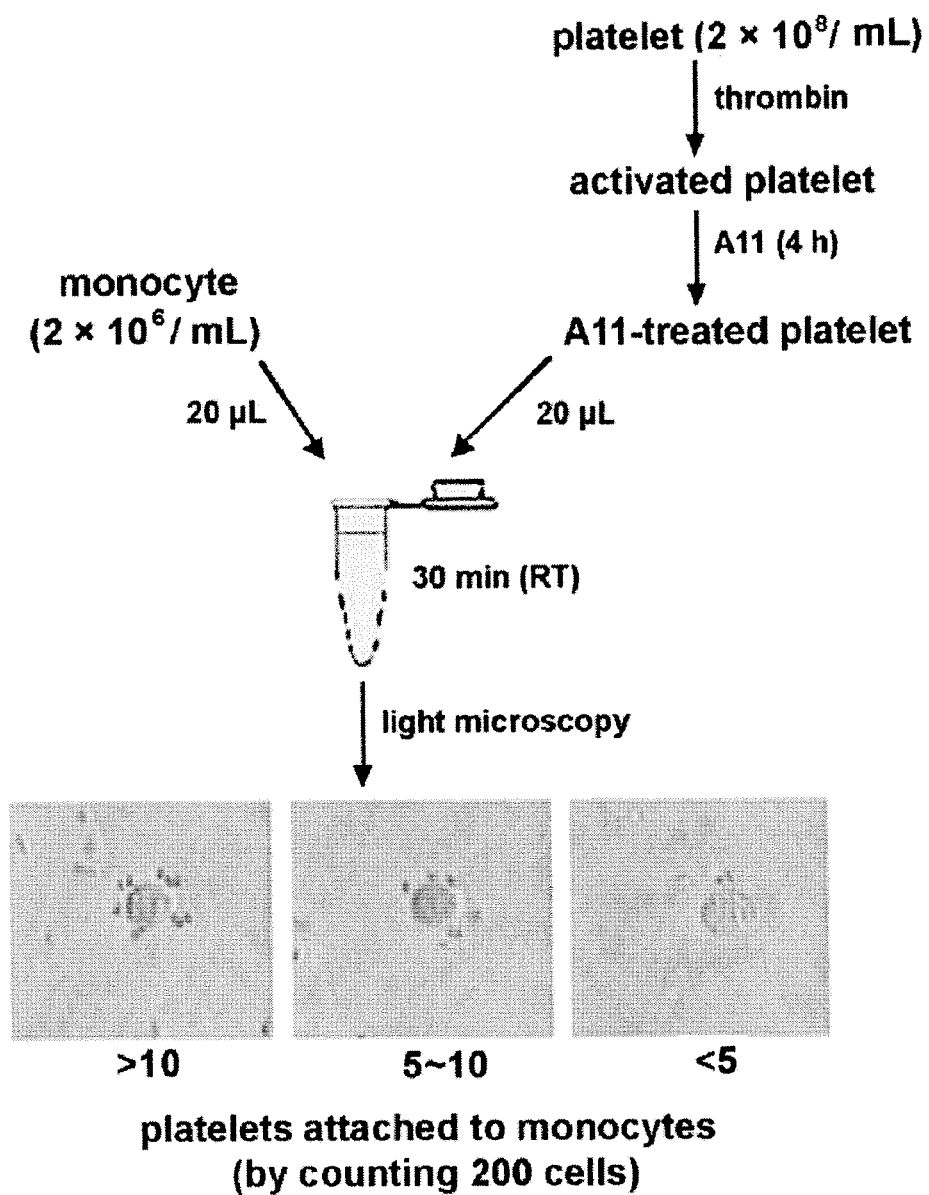
FIG. 7 depicts the protocol used to determine the interaction of activated platelets with monocytes. The percentage of monocytes observed to bind >10, 5~10, and <5 platelets was determined under phase microscopy (×400). The monocyte concentration was $2\times10^6$ cells/mL; the platelet concentration was $2\times10^8$ cells/mL. Various concentrations of scFv Abs (A11) were added as described in the methods.

The effect of A11 on the destruction of already formed tumor-platelet aggregates was investigated. FIG. 6F clearly demonstrates that A11 disaggregates thrombin-induced tumor-platelet clumps with a nadir at 4 hours, whereas control scFv (13CG2) had no effect. Since the adhesion of platelets to monocytes is also vital for tumor cell recruitment, the effect of A11 on the adherence between platelets and monocytes was also examined (FIG. 7 provides a illustration of the protocols utilized). As shown in Table 1, normally about 66% of monocytes are saturated with more than 10 activated platelets and about 31% contained between 5 to 10 attached platelets, with the remaining 3% containing only 5 or less attached platelets. However treatment of activated platelets with various concentration of A11 changed this distribution. The number of monocytes with less than 5 attached platelets increased from 3% to 29%, between 5 to 10 attached platelets increased from 31% to 57%, and the number of monocytes with more than 10 attached platelets dropped from 66% to 14%, after platelets were treated with A11. This suggests that A11 decreases the attachment of platelets to monocytes.

TABLE 1

Effects of A11 on the adhesive properties of thrombin activated platelets to human monocytes

| | | % Cell bound | |
|---|---|---|---|
| Concentration (μg/mL) | Attached plts (<5) | Attached plts (5-10) | Attached plts (>10) |
| A11  0 | 3% | 31% | 66% |
| 10 | 11% | 48% | 51% |
| 100 | 22% | 51% | 27% |
| 1000 | 29% | 57% | 14% |

Platelets (2 × 10⁸ cells/mL) were first activated by thrombin, and then incubated with various concentrations of A11 for 4 hours at 37° C. Twenty microliter of A11-treated activated platelets were added to an equal volume of human monocytes (2 × 106 cells/mL) and incubated at room temperature for 30 minutes followed by inspection and scoring of the monocytes with various numbers of attached platelets: monocytes with less than 5, between 5 to 10 and more than 10 attached platelets.

Example 7

Effect of A11 on the Biological Traits of Tumor Cells and Endothelial Cells

To rule out the possibility that A11 may be tumoricidal or cross-reactive with tumor cell antigens (for example human melanoma cells containing αvβ3), A11 was incubated with B16 melanoma cells and LLC cells for 7 days in vitro and cell death was evaluated using the MTT assay. No loss of viability could be detected for B16 (FIG. 8A) or LLC (FIG. 8B) cells at various concentrations of A11.

Figures 8A, 8B, 8C, 8D, 8E:
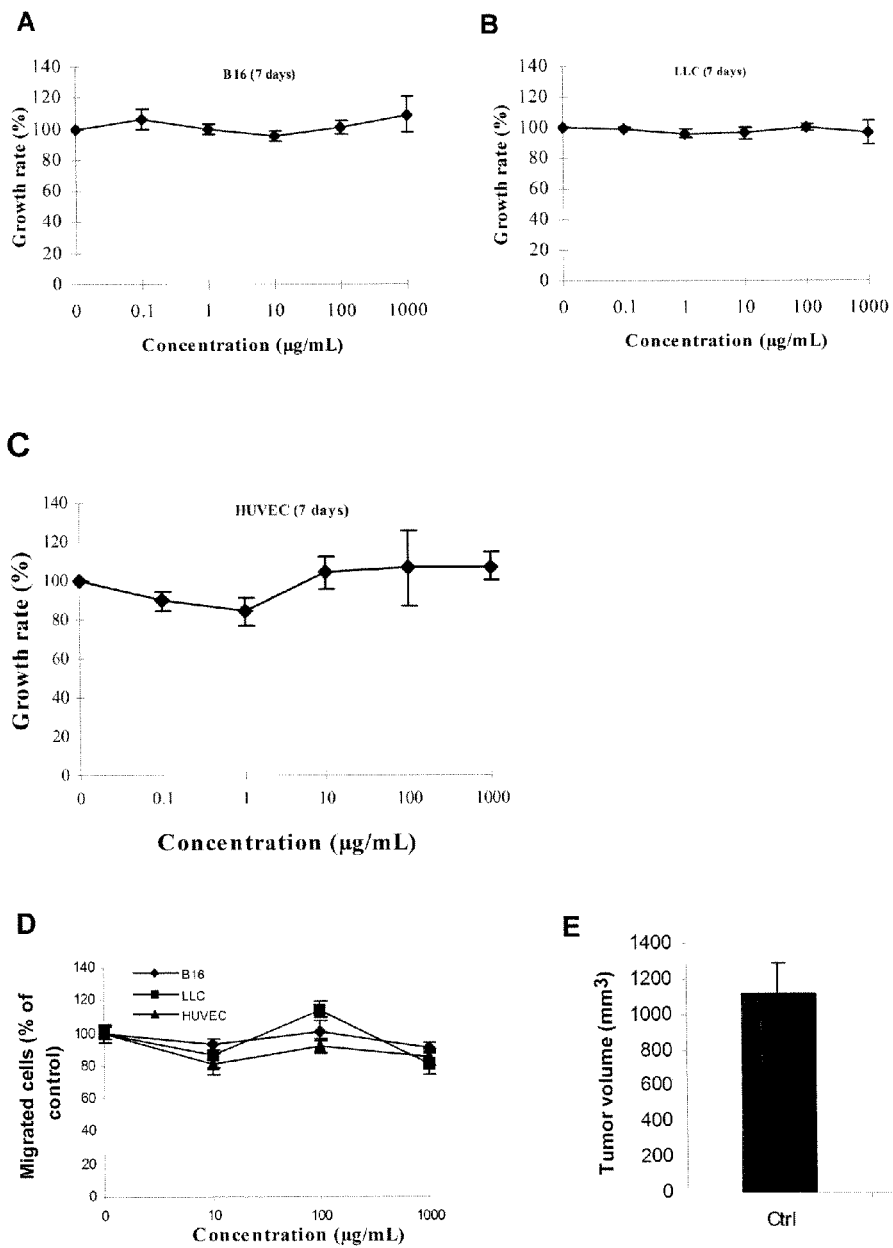
FIGS. 8A-8E show the effect of A11 on the viability of tumor cells and endothelial cells in vitro and in vivo.

Since endothelial integrin αvβ3 also shares the A11 epitope-bearing β3 chain, the effect of A11 on endothelial cell (HUVEC) was evaluated. In vitro, HUVECs grown in the presence of various concentrations of A11 for 7 days had no growth impairment (FIG. 8C). FIG. 8D shows that A11 had no effect on the chemotaxis of both tumor cells and HUVECs. A11 had no effect on s.c. LLC tumor growth compared to a saline control (FIG. 8E). Immunohistochemistry staining for CD31 demonstrated that the blood vessel density in the tumors of A11-treated mice had no significance difference compared to saline control. These results indicate that A11 had no effect on the biological traits of tumor cells and endothelial cells, precluding possible side-effects of A11 such as damaging endothelial cells.

Example 8

Effect of A11 on the Angiogenesis Process

Figures 9A, 9B:
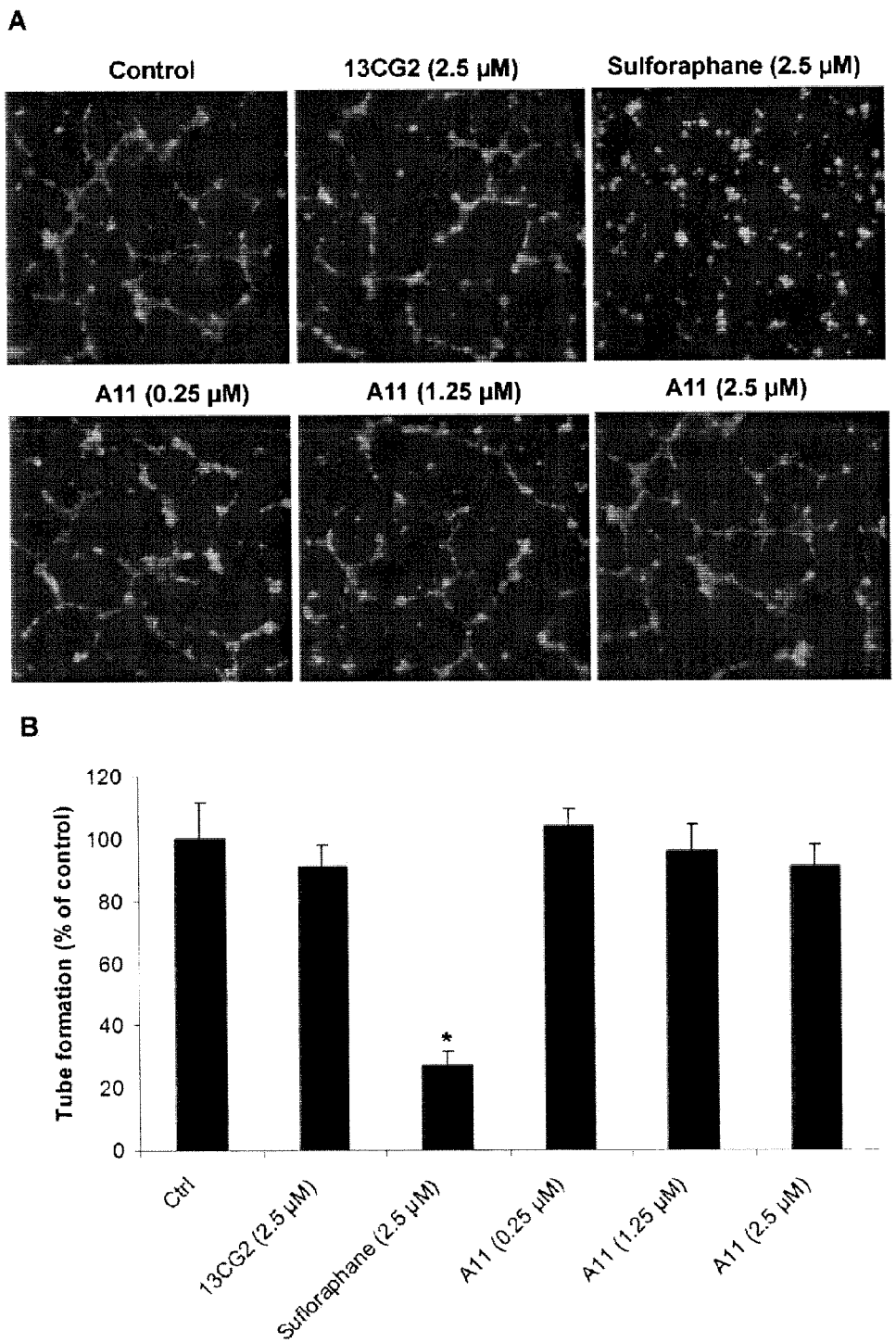
FIGS. 9A-9B shows the effect of A11 on HUVEC tube formation.
Figures 10A, 10B:
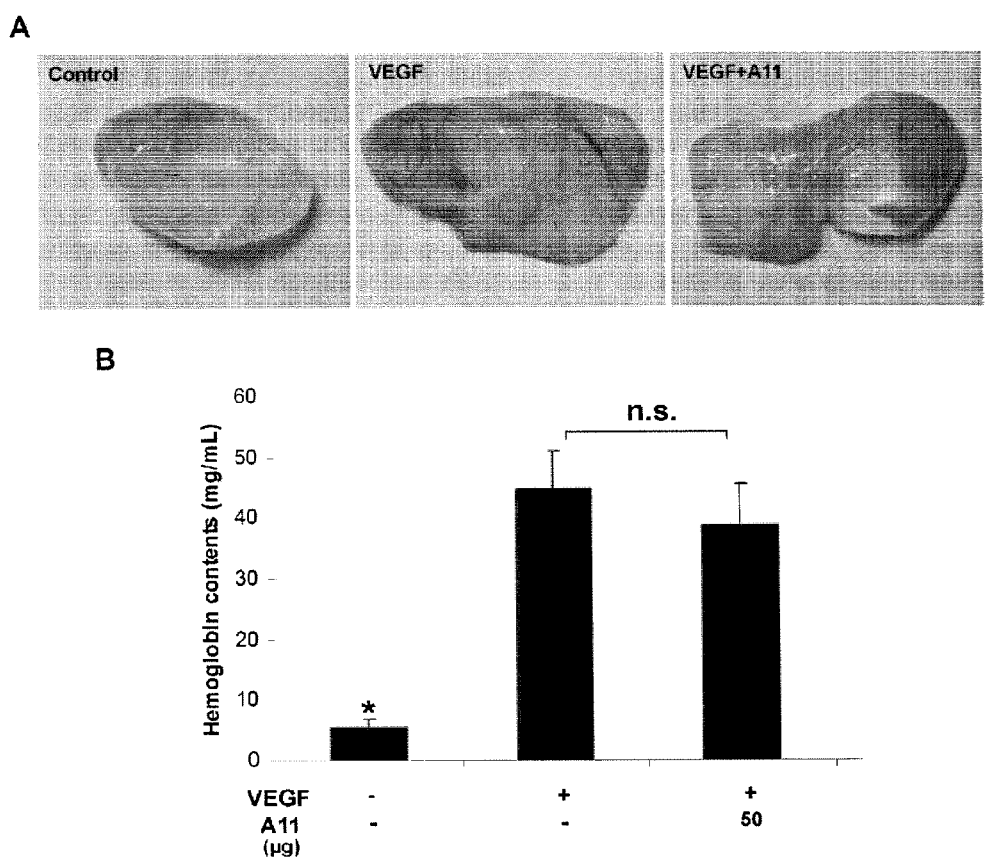
FIGS. 10A-10B show the effect of A11 on Matrigel plug in vivo angiogenesis. C57BL/6 mice were injected with 0.5 mL of Matrigel, with or without A11 (50 µg) and/or vascular endothelial growth factor (VEGF; 100 ng) and as labeled in the Figure. After 7 days, mice were killed and Matrigel plugs were excised.

In vitro, HUVECs form tube and capillary-like structures on the surface of basement membrane extract (Matrigel) in the presence of 50 ng/mL FGF-2 (Trevigen), through a process involving attachment, alignment, and migration. Treatment with different dose of A11 (0.25-2.5 μM) had no significant effect on this process (FIGS. 9A-9B). To determine whether A11 had an effect on VEGF-induced angiogenesis in vivo, the mouse Matrigel plug assay, an established in vivo angiogenesis model was used. Plugs with VEGF alone or mixed with 50 μg A11 appeared a similar red color, contrasting to plugs with Matrigel alone, which were pale in color, indicating no or reduced blood vessel formation (FIG. 10A). The vessels were abundantly filled with intact RBCs, which indicate the formation of a functional vasculature inside the Matrigel and blood circulation in newly formed vessels by the angiogenesis induced with VEGF. The Hb content inside the Matrigel plug was measured to quantify the effect of A11 on angiogenesis. It demonstrated that A11 had no effect on VEGF-induced neovessel formation in vivo (FIG. 10B).

Example 9

The Biological Safety of A11 In Vivo

Figures 11A, 11B:
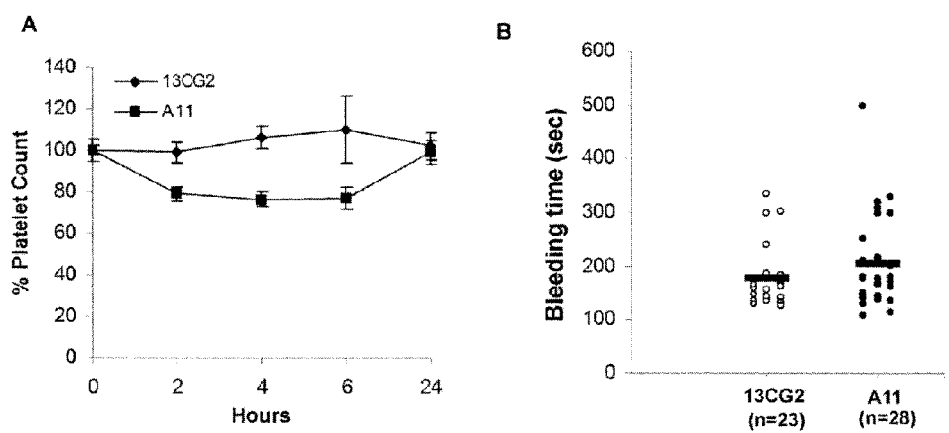
FIGS. 11A-11B show the effect of A11 on C57BL/6J mouse platelet count in vivo.

Previous studies had revealed that the greatest platelet drop induced by an optimal dose of A11 (25 μg/mouse) in BALB/c mice was at 4 hours (~18% platelet drop) with recovery to normal levels at 24 hours (Zhang et al., "Dissolution of Arterial Platelet Thrombi In Vivo with a Bifunctional Platelet GPIIIa49-66 Ligand which Specifically Targets the Platelet Thrombus," Blood 116(13):2336-2344 (2010), which is hereby incorporated by reference in its entirety). A similar effect was observed in C57BL/6J mice. FIG. 11 demonstrates that injection of the same dose of A11 (25 μg/mouse) resulted in an average 21% drop in the platelet count at the 4 hours post-injection time point (p<0.001 t=4 hours vs t=0). Injection of the same dose of control scFv Ab (13CG2) did not significantly affect the platelet count (p=0.8 t=4 hours vs t=0). FIG. 11B demonstrates that A11 had no significant effect on the mouse vein tail bleeding time 4 hours (nadir time point) compared to 13CG2 control (205±86 vs179±58; p=0.23). In addition, tumor-free C57BL/6J mice were given same dose of A11 at the same frequency as above and monitored daily for clinical signs of complications. A11-treated mice had no noticeable changes in fur, body weight, appetite, spontaneous bleeding, or life span. No significant pathologic changes were found in the heart, lung, liver, spleen, kidney, or brain by histologic examination. This suggests that the treatment is apparently harmless to mice.

Discussion of Examples 1-9

Cancer cells have been shown to aggregate platelets, and this ability correlates with the metastatic potential of cancer cells (Gasic, G. J., "Role of Plasma, Platelets, and Endothelial Cells in Tumor Metastasis," *Cancer Metastasis Rev.* 3(2):99-114 (1984); Karpatkin et al., "Role of Platelets in Tumor Cell Metastases," *Ann. NY Acad. Sci.* 370:101-118 (1981), which are hereby incorporated by reference in their entirety). The ability of malignant tumor cells to aggregate platelets is called tumor cell-induced platelet aggregation (TCIPA). There is strong evidence suggesting that platelet receptors, including GPIb-IX V, GPIIb/IIIa and P-selectin, are crucial for TCIPA (Karpatkin et al., "Role of Platelets in Tumor Cell Metastases," *Ann. NY Acad. Sci.* 370:101-118 (1981); Lonsdorf et al., "Engagement of alphaIIbbeta3 (GPIIb/IIIa) with alphanubeta3 Integrin Mediates Interaction of Melanoma Cells with Platelets: A Connection to Hematogenous Metastasis," *J. Biol. Chem.* 287(3):2168-2178 (2012), which are hereby incorporated by reference in their entirety). GPIIb/IIIa is especially implicated in TCIPA. Indeed antagonists of GPIIb/IIIa receptor are the most effective known inhibitors of TCIPA. Karpatkin et al., "Role of Adhesive Proteins in Platelet Tumor Interaction In Vitro and Metastasis Formation In Vitro," *J. Clin. Invest.* 81(4):1012-1019 (1988), which is hereby incorporated by reference in its entirety, first demonstrated that the drugs belonging to this group hold a potential to reduce TCIPA. A study using an oral GPIIb/IIIa antagonist, XV454, in a mouse model of experimental metastasis showed that this agent is able to inhibit lung metastases formation (Amirkhosravi et al., "Inhibition of Tumor Cell-Induced Platelet Aggregation and Lung Metastasis by the Oral GPIIb/IIIa Antagonist XV454," *Thromb. Haemost.* 90(3):549-554 (2003), which is hereby incorporated by reference in its entirety). Currently, a number of agents directed against human GPIIb/IIIa including abciximab, eptifibatide, and tirofiban have been evaluated in murine tumor models (Leclerc, J. R., "Platelet Glycoprotein IIb/IIIa Antagonists: Lessons Learned from Clinical Trials and Future Directions," *Crit. Care Med.* 30(5):S332-340 (2002), which is hereby incorporated by reference in its entirety). However, the most challenging problem for the clinical use of antithrombotic approaches in cancer is their lack of selectivity. They affect both haemostasis and cancer-induced thrombosis, which results in severe bleeding complications. Furthermore, currently available antiplatelet drugs target prevention rather than the more clinically relevant issue of resolution of an existing platelet-tumor thrombus. Described herein is a novel antimetastatic strategy through preferential dissolution of activated platelets in the tumor microenvironment using a humanized anti GPIIIa49-66 scFv Ab, which has significant translational value since it avoids interfering with hemostasis and minimizes bleeding side effects.

The work herein demonstrates the following: (1) In the spontaneous LLC metastatic model, A11 treatment decreased the mean number of surface nodules (A11 vs control scFv 13CG2, 6.5±2.8 vs 18±4.3, *p<0.01), and reduced the mean nodule volume per lung (A11 vs control scFv 13CG2, 1.47±0.35 vs 3.45±0.64, *p<0.01). (2) In an experimental LLC metastatic model, A11 provided protection against lung metastases in a time window from 4 hours before to 4 hours after i.v. injection of tumor cells. (3) Similar protective effects were observed in experimental metastasis using B16 melanoma. Simultaneously injection of a GPIIIa49-66 albumin conjugate prevents the anti-tumor activity induced by A11. (4) In vitro, the number of tumor cells adhering to platelets, platelets adhesion to HUVECs, platelet mediated tumor cells adhesion to HUVECs, and platelets adhesion to monocytes is significantly decreased in the presence of A11. A11 disaggregates thrombin-induced platelet-tumor clumps, whereas control scFv (13CG2) has no effect. (5) A11 had no effect on the angiogenesis process using in vitro and in vivo Matrigel assays.

Thus, a new antimetastatic strategy is proposed through lysing activated platelets in the tumor microenvironment with humanized anti-GPIIIa49-66 scFv Ab. Compared to traditional anti-platelet drugs, which prevent thrombosis by inhibiting normal platelet function, including platelet adhesion, aggregation and activation, A11 has a different mechanism of action and has distinct properties. It has no effect on normal platelet function (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010), which is hereby incorporated by reference in its entirety). However, it can induce oxidative platelet fragmentation in the absence of complement activation via Ab activation of platelet nicotinamide adenine dinucleotide phosphate oxidase and lipoxygenase releasing reactive oxygen species (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010); Li et al., "Platelet Fragmentation Requires a Specific Structural Conformation of Human Monoclonal Antibody Against beta3 Integrin," *J. Biol. Chem.* 283(6):3224-3230 (2008); Dang et al., "A Humanized Single-Chain Variable Fragment Antibody Against beta3 Integrin in *Escherichia coli*," *Hybridoma* 30(6):543-548 (2011), which are hereby incorporated by reference in their entirety). More importantly, it preferentially binds to activated versus resting platelets since activated platelets display more GPIIbIIIa reactive receptors on the surface (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010); Li et al., "Platelet Fragmentation Requires a Specific Structural Conformation of Human Monoclonal Antibody Against beta3 Integrin," *J. Biol. Chem.* 283(6):3224-3230 (2008); Dang et al., "A Humanized Single-Chain Variable Fragment Antibody Against beta3 Integrin in *Escherichia coli*," *Hybridoma* 30(6):543-548 (2011), which are hereby incorporated by reference in their entirety), making it more likely to be clinically useful by avoiding an increased bleeding risk. In addition, the data clearly demonstrates that A11 can dissolve an already formed platelet-tumor thrombus, making it more clinically relevant for cancer treatment. A11 impairs the adhesion of tumor cells to activated platelets, weakens platelet mediated tumor-endothelium adhesion, and decreases the activated platelet numbers bound to monocytes. Each of these properties can additively help inhibit platelet-tumor thrombus formation.

The studies herein focused on the effect of A11 on activated platelet mediated adhesion between tumor cells and endothelial cells in vitro and in vivo. To demonstrate the anti-metastasis effect is due to activated platelet lysis rather than disruption of endothelial cell biological function, several experiments were designed and employed. A11 had no effect on HUVEC proliferation, chemotaxis, and tube formation. In the plug assay model of angiogenesis in vivo, A11 had no inhibitory effect on neovascularization.

This novel strategy confers a number of advantages for the prevention of tumor cell metastases. Firstly, tumor cells lacking an intact coat of platelets will lose their ability to evade the body's immune system. Secondly, fragmented platelets will lose their ability to shield cancerous cells from the high shear forces seen in flowing blood that could potentially damage tumor cells. Thirdly, lysing activated platelets could disaggregate already formed large tumor-platelet aggregates, which could embolize in the microvasculature to a new extravasation site. Fourthly, lysed platelets will lose their ability to facilitate the adhesion of tumor cells to the vascular endothelium, and to release of a number of growth factors that can stimulate tumor cell growth.

Of particular interest was the observation that injection of A11 4 hours before or after inoculation of tumor cells provided a protective effect against tumor metastases, whereas injection of A11 given 12 hours prior or post-inoculation of tumor cells did not decrease metastases. It is likely that platelets play a crucial role within the first 12 hours of tumor inoculation. Indeed, tumor cells have been found to spread within pulmonary microvessels 2-6 hours post-injection, where they were associated with platelets and fibrin clots (Amirkhosravi et al., "Inhibition of Tumor Cell-Induced Platelet Aggregation and Lung Metastasis by the Oral GPIIb/IIIa Antagonist XV454," *Thromb. Haemost.* 90(3):549-554 (2003), which is hereby incorporated by reference in its entirety). The data herein confirms this observation. Mice treated with A11 after inoculation of tumor cells have reduced early invasion of the lung.

Previous studies have revealed that the platelet drop nadir induced by patient anti-GPIIIa49-66 Ab or its mimic Ab occurs at 4 hours with a recovery to normal at 24 hours (Nardi et al., "Complement-Independent Peroxide-Induced Antibody Lysis of Platelets in HIV-1-Related Immune Thrombocytopenia," *Cell* 106(5):551-561 (2001); Nardi et al., "Complement-Independent Ab-Induced Peroxide Lysis of Platelets Requires 12-Lipoxygenase and a Platelet NADPH Oxidase Pathway," *J. Clin. Invest.* 113(7):973-980 (2004); Li et al., "Role of Molecular Mimicry to HIV-1 Peptides in HIV-1 Related Immunologic Thrombocytopenia," *Blood* 106(2):572-576 (2005); Zhang et al., "Specific Cross-Reaction of Anti-dsDNA Antibody with Platelet Integrin GPIIIa49-66," *Autoimmunity* 43(8):682-689 (2010); Zhang et al., "Role of Molecular Mimickry of Hepatitis C (HCV) Protein with Platelet GPIIIa in Hepatitis C-Related Thrombocytopenia," *Blood* 113(17):4086-4093 (2009), which are hereby incorporated by reference in their entirety). A11 had similar pharmacokinetic properties as the parental Ab (Zhang et al., "Dissolution of Arterial Platelet Thrombi In Vivo with a Bifunctional Platelet GPIIIa49-66 Ligand which Specifically Targets the Platelet Thrombus," *Blood* 116(13):2336-2344 (2010); Li et al., "Platelet Fragmentation Requires a Specific Structural Conformation of Human Monoclonal Antibody Against beta3 Integrin," *J. Biol. Chem.* 283(6):3224-3230 (2008); Dang et al., "A Humanized Single-Chain Variable Fragment Antibody Against beta3 Integrin in *Escherichia coli,*" *Hybridoma* 30(6):543-548 (2011), which are hereby incorporated by reference in their entirety). In this study, injection of an optimal dose of A11 (25 µg/mouse) resulted in a modest drop of the non-activated circulating platelet count (~21%) at the nadir timepoint, which resulted in no significant change in the C57BL/6J mouse vein bleeding time. There was no evidence of complications due to A11 injections in mice at the same frequency as used in the tumor treatments. The current data have established the concept of developing a novel approach to combat tumor metastasis by preferentially fragmenting activated platelets in the tumor microenvironment via A11 or compounds with similar properties.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of inhibiting tumor metastasis in a subject, said method comprising:

selecting a subject having a tumor that will be removed by surgery and administering to the selected subject an antibody or binding portion thereof which selectively binds to GPIIIa49-66 on activated platelets, and disaggregates activated platelet-tumor cell aggregates upon said binding, wherein said administering is carried out in conjunction with said surgery in an amount effective to inhibit tumor metastasis associated with said surgery.

2. The method of claim 1, wherein the antibody or binding portion thereof is an antibody or binding portion thereof raised against GPIIIa49-66.

3. The method of claim 1, wherein the antibody or binding portion thereof is a monoclonal antibody.

4. The method of claim 1, wherein GPIIIa49-66 comprises the amino acid sequence of SEQ ID NO: 1.

5. The method of claim 1, wherein said administering is carried out parenterally, intravenously, intramuscularly, intraperitoneally, transdermally, or buccally.

6. The method of claim 1, wherein the antibody is a single chain antibody.

7. The method of claim 6, wherein the single chain antibody is A11.

8. The method of claim 1, wherein the tumor is a lung tumor, breast tumor, kidney tumor, or gastrointestinal tract tumor.

9. The method of claim 1, wherein said administering is carried out within four hours of surgery.

10. The method of claim 1, wherein said administering is carried out prior to said surgery, after said surgery, or both.

11. A method for inhibiting primary tumor growth in a subject, said method comprising:
    selecting a subject having a primary tumor that will be removed by surgery, and
    administering to the selected subject an antibody or binding portion thereof which selectively binds to GPIIIa49-66 on activated platelets, and disaggregates activated platelet-tumor cell aggregates upon said binding, wherein said administering is carried out in conjunction with said surgery in an amount effective to inhibit primary tumor growth induced by said surgery.

12. The method of claim 11, wherein the primary tumor is selected from the group consisting of a lung tumor, a breast tumor, a kidney tumor, and a gastrointestinal tract tumor.

13. The method of claim 11 wherein the antibody or binding portion thereof is an antibody or binding portion thereof raised against GPIIIa49-66.

14. The method of claim 11, wherein the antibody or binding portion thereof is a monoclonal antibody.

15. The method of claim 11, wherein GPIIIa49-66 comprises the amino acid sequence of SEQ ID NO: 1.

16. The method of claim 11, wherein said administering is carried out parenterally, intravenously, intramuscularly, intraperitoneally, transdermally, or buccally.

17. The method of claim 11, wherein the antibody is a single chain antibody.

18. The method of claim 17, wherein the single chain antibody is A11.

19. The method of claim 11, wherein said administering is carried out within four hours of surgery.

20. The method of claim 11, wherein said administering is carried out prior to said surgery, after said surgery, or both.

* * * * *